(12) United States Patent
Bart et al.

(10) Patent No.: US 9,932,601 B2
(45) Date of Patent: Apr. 3, 2018

(54) INHIBITION OF SNL6 EXPRESSION FOR BIOFUEL PRODUCTION

(75) Inventors: Rebecca Bart, Berkeley, CA (US); Mawsheng Chern, Davis, CA (US); Pamela Ronald, Davis, CA (US); Miguel Vega-Sanchez, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 671 days.

(21) Appl. No.: 13/704,969

(22) PCT Filed: Jun. 17, 2011

(86) PCT No.: PCT/US2011/040941
§ 371 (c)(1),
(2), (4) Date: Mar. 7, 2013

(87) PCT Pub. No.: WO2011/160057
PCT Pub. Date: Dec. 22, 2011

(65) Prior Publication Data
US 2013/0160161 A1 Jun. 20, 2013

Related U.S. Application Data

(60) Provisional application No. 61/356,503, filed on Jun. 18, 2010.

(51) Int. Cl.
*C12N 15/82* (2006.01)
(52) U.S. Cl.
CPC ..... *C12N 15/8245* (2013.01); *C12N 15/8218* (2013.01); *C12N 15/8246* (2013.01)
(58) Field of Classification Search
None
See application file for complete search history.

(56) References Cited

U.S. PATENT DOCUMENTS

| 8,362,325 | B2 * | 1/2013 | Troukhan | ............. | C07K 14/415 |
|---|---|---|---|---|---|
| | | | | | 435/183 |
| 2004/0123343 | A1 * | 6/2004 | La Rosa et al. | .............. | 800/278 |
| 2006/0021088 | A1 | 1/2006 | Inze et al. | | |
| 2006/0260011 | A1 * | 11/2006 | Carter | ................ | C12N 15/8218 |
| | | | | | 800/285 |
| 2008/0235820 | A1 * | 9/2008 | Sticklen | ............. | C12N 15/8218 |
| | | | | | 800/275 |
| 2009/0222953 | A1 * | 9/2009 | Tominaga | .......... | C12N 15/8261 |
| | | | | | 800/290 |

FOREIGN PATENT DOCUMENTS

WO WO 2009/157000 A1 12/2009

OTHER PUBLICATIONS

Piquemal et al, The Plant Journal (1998) 13: 71-83.*
The International Rice Genome Sequencing Project (2005) Nature 436: 793-800.*
Bart et al, 2010, PLoS Genetics, 6:1-10.*
Bart et al.; "Rice Snl6, a Cinnomoyl-CoA Reductase-Like Gene Family Member, Is Required for NH1-Mediaited Immunity to *Xanthomonas oryzae* pv. *oryzae*"; *PLoS Genetics*; 6(9):1-10 (Sep. 2010).
Kawasaki et al.; "Cinnamoyl-CoA reductase, a key enzyme in lignin biosynthesis, is an effector of small GTPase Rac in defense signaling in rice"; *Proc. Natl. Acad. Sci. USA*; 103(1):230-235 (Jan. 2006).
International Search Report from PCT/US2011/040941, dated Nov. 7, 2011.

* cited by examiner

*Primary Examiner* — Jason Deveau Rosen
(74) *Attorney, Agent, or Firm* — Kilpatrick Townsend & Stockton LLP

(57) ABSTRACT

The invention provides compositions and methods for inhibiting the expression of the gene Snl6 in plants. Plants with inhibited expression of Snl6 have use in biofuel production, e.g., by increasing the amount of soluble sugar that can be extracted from the plant.

9 Claims, 15 Drawing Sheets

A

B

Phylogram

| Sequence 1 | Sequence 2 | Score |
|---|---|---|
| Snl6 | Sorghum | 86 |
| Snl6 | Maize | 82 |
| Snl6 | Brachypodium | 81 |
| Snl6 | Os05g50250 | 73 |
| Snl6 | AT5G14700 | 44 |
| Snl6 | OsCCR1 | 28 |
| Snl6 | AtCCR2 | 28 |
| Snl6 | PtCCR | 28 |
| Snl6 | PvCCR1a | 27 |
| Snl6 | PvCCR2a | 27 |
| Snl6 | AtCCR1 | 25 |

Complete list of deleted genes in *snl6-FN*.

| | Locus ID | TIGR Annotation |
|---|---|---|
| Deletion 1A (57 kbp) | Os01g21370 | Transposon protein, putative |
| | Os01g21380 | FAD dependent oxidoreductase domain containing protein, expressed |
| | Os01g21390 | Hypothetical Protein |
| | Os01g21400 | Retrotransposon putative |
| | Os01g21410 | Expressed Protein |
| | Os01g21420 | pre-mRNA-splicing factor SF2, expressed |
| | Os01g21430 | Retrotransposon protein, putative, Ty3-gypsy subclass |
| | Os01g21440 | Expressed Protein |
| | Os01g21450 | Expressed Protein |
| | Os01g21480 | Transposon protein, putative, CACTA, En/Spm sub-class |
| Deletion 1B (13.5 kbp) | Os01g45160 | Conserved hypothetical protein |
| | Os01g45174 | transposon protein, putative |
| | Os01g45190 | DEAD-box ATP-dependent RNA helicase, putative, expressed |
| | Os01g45200 | Cinnamoyl-CoA reductase-related, putative, expressed |
| | Os01g45210 | Retrotransposon protein, putative, Ty3-gypsy subclass |
| | Os01g45220 | Retrotransposon protein, putative, Ty3-gypsy subclass |
| Deletion 2 (3 kbp) | Os02g33730 | Ubiquinol-cytochrome C reductase hinge protein, putative, expressed |
| Deletion 3 (100.5 kbp) | Os03g56070 | Expressed Protein |
| | Os03g56080 | Hypothetical Protein |
| | Os03g56090 | MYB family transcription factor, putative, expressed |
| | Os03g56100 | hypothetical protein |
| | Os03g56110 | Homeobox protein knotted-1, putative, expressed |
| | Os03g56120 | Hypothetical Protein |
| | Os03g56130 | Lichenase-2 precursor, putative |
| | Os03g56140 | Homeobox protein rough sheath 1, putative expressed |
| | Os03g56149 | Hypothetical Protein |
| | Os03g56160 | Lectin-like receptor kinase 7, putative, expressed |
| | Os03g56170 | Conserved hypothetical protein |
| | Os03g56180 | Legume lectins beta domain containing protein, expressed |
| | Os03g56190 | Cytochrome c oxidase-related, putative, expressed |
| | Os03g56200 | Expressed Protein |
| | Os03g56220 | Stress-induced protein, putative, expressed |
| | Os03g56234 | myb/SANT domain protein, putative, expressed |
| | Os03g56241 | 40S ribosomal protein S29, putative, expressed |
| Deletion (6 kbp) | Os07g35810 | TKL_IRAK_DUF26-ld.6 - kinase, expressed |

*FIG. 14*

```
Sorghum      ------------------------------------MGVLRSTQSLQAEVDELRAALG  22
maize        ------------------------------------MGVLRSTQSLEAEVDELRAAL-  21
Snl6         -----------------------------------MRAALLHGHGGGAAAAA--      17
Brachypodium NFANHTPPPGTTPPGETSSLQEGRAPAGVAASSRARGGMGVLRSTQSLQAEVEEMRAALL  60
Os05g50250   ------------------------------------MGVLRSTQSMEAEVEEMRAALA  22

Sorghum      LSGGGGHGEAAAGGGWRRSAGRGHADAKRAPGGDAGAGAAARAVCVTGGISFVGFAVVDR  82
maize        -----------LAGGWRRSAG--HADAKRAPRGDAG-GAAARAVCVTGGISFVGFAVVDR  67
Snl6         -----------AAGWRPSAG--DADVKRTAGGDGG-AAGPRTVCVTGGISFVGFAVVDR  62
Brachypodium LPGG-------AAAGWKPSGG--------DAGGEEG-AAGPRTVCVTGGISFVGFAIVDR 104
Os05g50250   LAPLG------RHGAWRSGAA-----AKREAGAEEGAAPEARTVCVTGGISFVGLAVVDR  71
                                                  :  ****. .::.   :*.

Sorghum      LLRHGYTVRLALETQEDMDKLREMEMFGE--DGRDG-VWTVMANVMDPESLHRAFDGCAG 139
maize        LLRHGYTVRLALETQEDMDKLREMEMFGE--DGRDGGVSTVMANVMDPDGLRRAFDGCAG 125
Snl6         LLRHGYTVRLALETQEDLDKLREMEMFGE--DGRDG-VWTVMANVTDPESLHRAFDGCAG 119
Brachypodium LLRQGYTVRLALETQEDVDKLREMEMFGE--DGRDG-VWTVMANVMDPESLHRAFDGCAG 161
Os05g50250   LLRHGYAVRLALETQEDLDKLREMEMFGE--NGRDG-VWTVMANVMDPESLNQAFNGCVG 128
             ** :** *: .    * .:      .       :     : : :  .:   ..** *

Sorghum      VFHTSAFVDPGGMSGYTKHM-ATLEAQAAERVIEACVRTESVRKCVFTSSLLACVWRQNY 198
maize        VFHTSAFVDPGGMSGYTKHM-AALEAQAAERVIEACVRTESVRKCVFTSSLLACVWRQDY 184
Snl6         VFHTSAFVDPGGMSGYTKHM-ASLEAKAAEQVIEACVRTESVRKCVFTSSLLACVWRQNY 178
Brachypodium VFHTSAFVDPGGMSGYTKHM-ASLEAKAAERVIETCVRTESVRKCIFTSSLLACVWRQNY 220
Os05g50250   VFHTSSLIDPGGISGYTKHM-AILEARAAEQVVEACVRTESVRKCVFTSSLLACVWRQSY 187
             ***.::  :              ..  :. *:  :..   *:: ::*** *     .

Sorghum      PHDRR-CPTIIDESCWSDESFCRDNKLWFALGKTAAEKAAWRAARGRDLKLVTICPALVT 257
maize        PHDRR-CPTTIDESCWSDESFCRDNKLWFALGKTAAEKAAWRAARGRDLKLVTICPALVT 243
Snl6         PHDRR-FPTIIDENCWSDESFCRDNKLWFALGKTAAEKTAWRAARGRDLKLVTVCPALVT 237
Brachypodium PHDRR-GPSIIDENCWSDESFCRDNKLWFALGKTAAEKAAWRAARGRDLKLVTVCPALVT 279
Os05g50250   PHHRRRFPAIIDESCWSDESFCRDNKLWFALGKTMAEKAAWRAARGRDLKLVTICPALVT 247
              :  .*** .:*  .. :.  .* ** :*    * :::.*..: *   :

Sorghum      GPG---FRRRNSTASIAYLKG-ARAMLADGLLATANVETVAEAHVHAYEAM-GDNTAG-G 311
maize        GPG---FRRRNSTASIAYLKAGARAMLADGLLATANVETVAEAHVHAYEAM-GDNTAG-G 298
Snl6         GPG---FRRRNSTASIAYLKG-ARAMLADGLLATANVETVAEAHVRVYEAM-GDNTAG-G 291
Brachypodium GPG---FRRRNSTASIAYLKG-SRDMLAEGVLATANVETVAEAHVRAYEAM-GNNTAG-G 333
Os05g50250   GPG---FRRRNSTPSIAYLKG-AHAMLAEGLLATADVERVAEAHVRVYEAMSGGGAAG-G 302
             **         .    ** .: .  .:  .   *. :* .*:  :*        *  *

Sorghum      RYICYDHVVKRPEEFAELERQLGLPG-GATAARGS-DDDRP-----ARFELCK-RKLSRL 363
maize        RYICYDHVVKRPEEFAELERQLGLPG-GAAPAPAHGSDDRP-----ARFELCK-RKLSRL 351
Snl6         RYICYDHVVKRPEEFAELERQLGIPRRAAAAAAAQDSGDRP-----ARFDLCR-QKLARL 345
Brachypodium RYICYDHVIRRAEDFAELERQLGIPSRTAASVLQSGDEDRP-----ARFELCK-RKLARL 387
Os05g50250   RYICYDHVVRRGEEFAELQRQLGLPITGVAAASRPGYSDDGDVGGDGRFALCN-GKLARL 361
             *::     *  :    *  *  *  .  :                  :       .*

Sorghum      MSSRRRCTYDTYYSVAFD-------------------------- 381
maize        MSSRRRCAYDTYYSVAFEV------------------------- 370
Snl6         MSTRRRCTYDDYYSVAFD-------------------------- 363
Brachypodium MSSRRRCTYDDYYYSVTSP------------------------- 406
Os05g50250   VSSRRRCTYDVYYPASYD-------------------------- 379
              .   :.  .
```

*FIG. 15*

SEQUENCE LISTING

<160> NUMBER OF SEQ ID NOS: 38

<210> SEQ ID NO 1
<211> LENGTH: 1092
<212> TYPE: DNA
<213> ORGANISM: Oryza sativa
<220> FEATURE:
<223> OTHER INFORMATION: suppressor of NH1-mediated lesion formation 6
      (Snl6) cDNA, cinnamoyl-CoA reductase-like family

<400> SEQUENCE: 1

```
atgcgggcgg cgctgctgca tggccacggg ggcggggcgg cggcggcggc ggcggccggg     60
tggcgcccct cggccggcga cgcggacgtc aagcgcaccg cggcggcga cggggcgcg    120
gcggggccgc gcaccgtctg cgtcacgggc ggcatctcct tcgtcgggtt cgccgtcgtc    180
gaccgcctgc tccggcacgg ctacaccgtg cgcctcgccc tcgagaccca agaggacctg    240
gacaagctga gggagatgga gatgttcggc gaggacggcc gggacggcgt gtggacggtg    300
atggcgaacg tgacggaccc cgagagcctg caccgggcgt cgacggatg cgccggcgtg    360
tttcacacct cggcgttcgt ggatccgggg ggcatgtccg gctacacgaa acatatggca    420
agcttggagg cgaaagcagc agagcaggtg atcgaggcgt gcgtgaggac agagtccgtc    480
agaaaatgcg tcttcacgtc gtcgttgcta gcatgtgtat ggaggcaaaa ttaccctcat    540
gaccgacggt ttcctaccat catcgacgag aactgctgga gcgatgagag cttctgccgt    600
gacaacaagc tgtggttttgc actgggcaag acggcagcgg agaagacggc gtggagggca    660
gccaggggta gggacctgaa gctggtcacc gtctgcccgg cgctggtcac cggtccggga    720
ttccgccgcc gcaactccac cgcctccatc gcctacctca aggggctcg cgccatgctc    780
gccgacggcc tgctcgcgac ggcgagcgtg gagacggtgg cggaggcgca cgtccgggtg    840
tacgaggcga tgggcgacaa cacggccggc gggaggtaca tctgctacga ccacgtggtg    900
aagaggcccg aggagttcgc ggagctggag cgccagctgg ggatcccgcg cagagcggcg    960
gcggcggcgg ccgcgcagga ctccggcgac cggccggcga ggttcgatct gtgcaggcag   1020
aagctggcga ggctcatgtc cacccgaagg cggtgcacgt acgacgacta ctactccgtc   1080
gcattcgact ag                                                       1092
```

<210> SEQ ID NO 2
<211> LENGTH: 363
<212> TYPE: PRT
<213> ORGANISM: Oryza sativa
<220> FEATURE:
<223> OTHER INFORMATION: suppressor of NH1-mediated lesion formation 6
      (Snl6), cinnamoyl-CoA reductase-like family

<400> SEQUENCE: 2

```
Met Arg Ala Ala Leu Leu His Gly His Gly Gly Ala Ala Ala Ala
  1               5                  10                  15

Ala Ala Ala Gly Trp Arg Pro Ser Ala Gly Asp Ala Asp Val Lys Arg
             20                  25                  30

Thr Ala Gly Gly Asp Gly Gly Ala Ala Gly Pro Arg Thr Val Cys Val
         35                  40                  45
```

```
Thr Gly Gly Ile Ser Phe Val Gly Phe Ala Val Val Asp Arg Leu Leu
    50                  55                  60

Arg His Gly Tyr Thr Val Arg Leu Ala Leu Glu Thr Gln Glu Asp Leu
65                  70                  75                  80

Asp Lys Leu Arg Glu Met Glu Met Phe Gly Glu Asp Gly Arg Asp Gly
                85                  90                  95

Val Trp Thr Val Met Ala Asn Val Thr Asp Pro Glu Ser Leu His Arg
            100                 105                 110

Ala Phe Asp Gly Cys Ala Gly Val Phe His Thr Ser Ala Phe Val Asp
        115                 120                 125

Pro Gly Gly Met Ser Gly Tyr Thr Lys His Met Ala Ser Leu Glu Ala
    130                 135                 140

Lys Ala Ala Glu Gln Val Ile Glu Ala Cys Val Arg Thr Glu Ser Val
145                 150                 155                 160

Arg Lys Cys Val Phe Thr Ser Ser Leu Leu Ala Cys Val Trp Arg Gln
                165                 170                 175

Asn Tyr Pro His Asp Arg Arg Phe Pro Thr Ile Ile Asp Glu Asn Cys
            180                 185                 190

Trp Ser Asp Glu Ser Phe Cys Arg Asp Asn Lys Leu Trp Phe Ala Leu
        195                 200                 205

Gly Lys Thr Ala Ala Glu Lys Thr Ala Trp Arg Ala Ala Arg Gly Arg
    210                 215                 220

Asp Leu Lys Leu Val Thr Val Cys Pro Ala Leu Val Thr Gly Pro Gly
225                 230                 235                 240

Phe Arg Arg Arg Asn Ser Thr Ala Ser Ile Ala Tyr Leu Lys Gly Ala
                245                 250                 255

Arg Ala Met Leu Ala Asp Gly Leu Leu Ala Thr Ala Ser Val Glu Thr
            260                 265                 270

Val Ala Glu Ala His Val Arg Val Tyr Glu Ala Met Gly Asp Asn Thr
        275                 280                 285

Ala Gly Gly Arg Tyr Ile Cys Tyr Asp His Val Val Lys Arg Pro Glu
    290                 295                 300

Glu Phe Ala Glu Leu Glu Arg Gln Leu Gly Ile Pro Arg Arg Ala Ala
305                 310                 315                 320

Ala Ala Ala Ala Ala Gln Asp Ser Gly Asp Arg Pro Ala Arg Phe Asp
                325                 330                 335

Leu Cys Arg Gln Lys Leu Ala Arg Leu Met Ser Thr Arg Arg Arg Cys
            340                 345                 350

Thr Tyr Asp Asp Tyr Tyr Ser Val Ala Phe Asp
        355                 360

<210> SEQ ID NO 3
<211> LENGTH: 381
<212> TYPE: PRT
<213> ORGANISM: Sorghum bicolor
<220> FEATURE:
<223> OTHER INFORMATION: sorghum Snl6 homolog, GenBank Accession No.
      EES03334.1

<400> SEQUENCE: 3

Met Gly Val Leu Arg Ser Thr Gln Ser Leu Gln Ala Glu Val Asp Glu
 1               5                  10                  15

Leu Arg Ala Ala Leu Gly Leu Ser Gly Gly Gly His Gly Glu Ala
            20                  25                  30

Ala Ala Gly Gly Gly Trp Arg Arg Ser Ala Gly Arg Gly His Ala Asp
        35                  40                  45
```

Ala Lys Arg Ala Pro Gly Gly Asp Ala Gly Ala Ala Arg
    50              55              60

Ala Val Cys Val Thr Gly Gly Ile Ser Phe Val Gly Phe Ala Val Val
65              70              75              80

Asp Arg Leu Leu Arg His Gly Tyr Thr Val Arg Leu Ala Leu Glu Thr
                85              90              95

Gln Glu Asp Met Asp Lys Leu Arg Glu Met Glu Met Phe Gly Glu Asp
            100             105             110

Gly Arg Asp Gly Val Trp Thr Val Met Ala Asn Val Met Asp Pro Glu
        115             120             125

Ser Leu His Arg Ala Phe Asp Gly Cys Ala Gly Val Phe His Thr Ser
    130             135             140

Ala Phe Val Asp Pro Gly Gly Met Ser Gly Tyr Thr Lys His Met Ala
145             150             155             160

Thr Leu Glu Ala Gln Ala Ala Glu Arg Val Ile Glu Ala Cys Val Arg
                165             170             175

Thr Glu Ser Val Arg Lys Cys Val Phe Thr Ser Ser Leu Leu Ala Cys
            180             185             190

Val Trp Arg Gln Asn Tyr Pro His Asp Arg Arg Cys Pro Thr Ile Ile
        195             200             205

Asp Glu Ser Cys Trp Ser Asp Glu Ser Phe Cys Arg Asp Asn Lys Leu
    210             215             220

Trp Phe Ala Leu Gly Lys Thr Ala Ala Glu Lys Ala Ala Trp Arg Ala
225             230             235             240

Ala Arg Gly Arg Asp Leu Lys Leu Val Thr Ile Cys Pro Ala Leu Val
                245             250             255

Thr Gly Pro Gly Phe Arg Arg Arg Asn Ser Thr Ala Ser Ile Ala Tyr
            260             265             270

Leu Lys Gly Ala Arg Ala Met Leu Ala Asp Gly Leu Leu Ala Thr Ala
        275             280             285

Asn Val Glu Thr Val Ala Glu Ala His Val His Ala Tyr Glu Ala Met
    290             295             300

Gly Asp Asn Thr Ala Gly Gly Arg Tyr Ile Cys Tyr Asp His Val Val
305             310             315             320

Lys Arg Pro Glu Glu Phe Ala Glu Leu Glu Arg Gln Leu Gly Leu Pro
                325             330             335

Gly Gly Ala Thr Ala Ala Arg Gly Ser Asp Asp Arg Pro Ala Arg
            340             345             350

Phe Glu Leu Cys Lys Arg Lys Leu Ser Arg Leu Met Ser Ser Arg Arg
        355             360             365

Arg Cys Thr Tyr Asp Thr Tyr Tyr Ser Val Ala Phe Asp
    370             375             380

<210> SEQ ID NO 4
<211> LENGTH: 370
<212> TYPE: PRT
<213> ORGANISM: Zea mays
<220> FEATURE:
<223> OTHER INFORMATION: maize Snl6 homolog, GenBank Accession No.
      ACR34585.1

<400> SEQUENCE: 4

Met Gly Val Leu Arg Ser Thr Gln Ser Leu Glu Ala Glu Val Asp Glu
1               5               10              15

Leu Arg Ala Ala Leu Leu Ala Gly Gly Trp Arg Arg Ser Ala Gly His

```
            20                  25                  30
Ala Asp Ala Lys Arg Ala Pro Arg Gly Asp Ala Gly Gly Ala Ala
        35                  40                  45
Arg Ala Val Cys Val Thr Gly Gly Ile Ser Phe Val Gly Phe Ala Val
 50                  55                  60
Val Asp Arg Leu Leu Arg His Gly Tyr Thr Val Arg Leu Ala Leu Glu
 65                  70                  75                  80
Thr Gln Glu Asp Met Asp Lys Leu Arg Glu Met Glu Met Phe Gly Glu
                 85                  90                  95
Asp Gly Arg Asp Gly Gly Val Ser Thr Val Met Ala Asn Val Met Asp
                100                 105                 110
Pro Asp Gly Leu Arg Arg Ala Phe Asp Gly Cys Ala Gly Val Phe His
                115                 120                 125
Thr Ser Ala Phe Val Asp Pro Gly Gly Met Ser Gly Tyr Thr Lys His
            130                 135                 140
Met Ala Ala Leu Glu Ala Gln Ala Ala Glu Arg Val Ile Glu Ala Cys
145                 150                 155                 160
Val Arg Thr Glu Ser Val Arg Lys Cys Val Phe Thr Ser Ser Leu Leu
                165                 170                 175
Ala Cys Val Trp Arg Gln Asp Tyr Pro His Asp Arg Arg Cys Pro Thr
            180                 185                 190
Thr Ile Asp Glu Ser Cys Trp Ser Asp Glu Ser Phe Cys Arg Asp Asn
            195                 200                 205
Lys Leu Trp Phe Ala Leu Gly Lys Thr Ala Ala Glu Lys Ala Ala Trp
        210                 215                 220
Arg Ala Ala Arg Gly Arg Asp Leu Lys Leu Val Thr Ile Cys Pro Ala
225                 230                 235                 240
Leu Val Thr Gly Pro Gly Phe Arg Arg Arg Asn Ser Thr Ala Ser Ile
                245                 250                 255
Ala Tyr Leu Lys Ala Gly Ala Arg Ala Met Leu Ala Asp Gly Leu Leu
            260                 265                 270
Ala Thr Ala Asn Val Glu Thr Val Ala Glu His Val His Ala Tyr
            275                 280                 285
Glu Ala Met Gly Asp Asn Thr Ala Gly Gly Arg Tyr Ile Cys Tyr Asp
        290                 295                 300
His Val Val Lys Arg Pro Glu Glu Phe Ala Glu Leu Glu Arg Gln Leu
305                 310                 315                 320
Gly Leu Pro Gly Gly Ala Ala Pro Ala Pro Ala His Gly Ser Asp Asp
                325                 330                 335
Arg Pro Ala Arg Phe Glu Leu Cys Lys Arg Lys Leu Ser Arg Leu Met
            340                 345                 350
Ser Ser Arg Arg Arg Cys Ala Tyr Asp Thr Tyr Tyr Ser Val Ala Phe
            355                 360                 365
Glu Val
    370

<210> SEQ ID NO 5
<211> LENGTH: 406
<212> TYPE: PRT
<213> ORGANISM: Brachypodium sp.
<220> FEATURE:
<223> OTHER INFORMATION: Brachypodium Snl6 homolog, Brachypodium
      Sequence Resource Accession No. Bradi2g44800.1

<400> SEQUENCE: 5
```

```
Asn Phe Ala Asn His Thr Pro Pro Gly Thr Thr Pro Pro Gly Glu
 1               5                  10                  15

Thr Ser Ser Leu Gln Glu Gly Arg Ala Pro Ala Gly Val Ala Ala Ser
             20                  25                  30

Ser Arg Ala Arg Gly Gly Met Gly Val Leu Arg Ser Thr Gln Ser Leu
         35                  40                  45

Gln Ala Glu Val Glu Glu Met Arg Ala Ala Leu Leu Leu Pro Gly Gly
     50                  55                  60

Ala Ala Gly Trp Lys Pro Ser Gly Gly Asp Ala Gly Gly Glu
 65              70                  75                  80

Gly Ala Ala Gly Pro Arg Thr Val Cys Val Thr Gly Gly Ile Ser Phe
                 85                  90                  95

Val Gly Phe Ala Ile Val Asp Arg Leu Leu Arg Gln Gly Tyr Thr Val
             100                 105                 110

Arg Leu Ala Leu Glu Thr Gln Glu Asp Val Asp Lys Leu Arg Glu Met
             115                 120                 125

Glu Met Phe Gly Glu Asp Gly Arg Asp Gly Val Trp Thr Val Met Ala
         130                 135                 140

Asn Val Met Asp Pro Glu Ser Leu His Arg Ala Phe Asp Gly Cys Ala
145                 150                 155                 160

Gly Val Phe His Thr Ser Ala Phe Val Asp Pro Gly Gly Met Ser Gly
                 165                 170                 175

Tyr Thr Lys His Met Ala Ser Leu Glu Ala Lys Ala Ala Glu Arg Val
             180                 185                 190

Ile Glu Thr Cys Val Arg Thr Glu Ser Val Arg Lys Cys Ile Phe Thr
         195                 200                 205

Ser Ser Leu Leu Ala Cys Val Trp Arg Gln Asn Tyr Pro His Asp Arg
     210                 215                 220

Arg Gly Pro Ser Ile Ile Asp Glu Asn Cys Trp Ser Asp Glu Ser Phe
225                 230                 235                 240

Cys Arg Asp Asn Lys Leu Trp Phe Ala Leu Gly Lys Thr Ala Ala Glu
                 245                 250                 255

Lys Ala Ala Trp Arg Ala Ala Arg Gly Arg Asp Leu Lys Leu Val Thr
             260                 265                 270

Val Cys Pro Ala Leu Val Thr Gly Pro Gly Phe Arg Arg Asn Ser
         275                 280                 285

Thr Ala Ser Ile Ala Tyr Leu Lys Gly Ser Arg Asp Met Leu Ala Glu
     290                 295                 300

Gly Val Leu Ala Thr Ala Asn Val Glu Thr Val Ala Glu Ala His Val
305                 310                 315                 320

Arg Ala Tyr Glu Ala Met Gly Asn Asn Thr Ala Gly Gly Arg Tyr Ile
                 325                 330                 335

Cys Tyr Asp His Val Ile Arg Arg Ala Glu Asp Phe Ala Glu Leu Glu
             340                 345                 350

Arg Gln Leu Gly Ile Pro Ser Arg Thr Ala Ala Ser Val Leu Gln Ser
         355                 360                 365

Gly Asp Glu Asp Arg Pro Ala Arg Phe Glu Leu Cys Lys Arg Lys Leu
     370                 375                 380

Ala Arg Leu Met Ser Ser Arg Arg Arg Cys Thr Tyr Asp Asp Tyr Tyr
385                 390                 395                 400

Tyr Ser Val Thr Ser Pro
                 405
```

<210> SEQ ID NO 6
<211> LENGTH: 379
<212> TYPE: PRT
<213> ORGANISM: Oryza sativa
<220> FEATURE:
<223> OTHER INFORMATION: rice locus ID Os05g50250

<400> SEQUENCE: 6

```
Met Gly Val Leu Arg Ser Thr Gln Ser Met Glu Ala Glu Val Glu Glu
  1               5                  10                  15

Met Arg Ala Ala Leu Ala Leu Ala Pro Leu Gly Arg His Gly Ala Trp
             20                  25                  30

Arg Ser Gly Ala Ala Ala Lys Arg Glu Ala Gly Ala Glu Glu Gly Ala
         35                  40                  45

Ala Pro Glu Ala Arg Thr Val Cys Val Thr Gly Gly Ile Ser Phe Val
     50                  55                  60

Gly Leu Ala Val Val Asp Arg Leu Leu Arg His Gly Tyr Ala Val Arg
 65                  70                  75                  80

Leu Ala Leu Glu Thr Gln Glu Asp Leu Asp Lys Leu Arg Glu Met Glu
                 85                  90                  95

Met Phe Gly Glu Asn Gly Arg Asp Gly Val Trp Thr Val Met Ala Asn
            100                 105                 110

Val Met Asp Pro Glu Ser Leu Asn Gln Ala Phe Asn Gly Cys Val Gly
        115                 120                 125

Val Phe His Thr Ser Ser Leu Ile Asp Pro Gly Gly Ile Ser Gly Tyr
    130                 135                 140

Thr Lys His Met Ala Ile Leu Glu Ala Arg Ala Ala Glu Gln Val Val
145                 150                 155                 160

Glu Ala Cys Val Arg Thr Glu Ser Val Arg Lys Cys Val Phe Thr Ser
                165                 170                 175

Ser Leu Leu Ala Cys Val Trp Arg Gln Ser Tyr Pro His His Arg Arg
            180                 185                 190

Arg Phe Pro Ala Ile Ile Asp Glu Ser Cys Trp Ser Asp Glu Ser Phe
        195                 200                 205

Cys Arg Asp Asn Lys Leu Trp Phe Ala Leu Gly Lys Thr Met Ala Glu
    210                 215                 220

Lys Ala Ala Trp Arg Ala Ala Arg Gly Arg Asp Leu Lys Leu Val Thr
225                 230                 235                 240

Ile Cys Pro Ala Leu Val Thr Gly Pro Gly Phe Arg Arg Arg Asn Ser
                245                 250                 255

Thr Pro Ser Ile Ala Tyr Leu Lys Gly Ala His Ala Met Leu Ala Glu
            260                 265                 270

Gly Leu Leu Ala Thr Ala Asp Val Glu Arg Val Ala Glu Ala His Val
        275                 280                 285

Arg Val Tyr Glu Ala Met Ser Gly Gly Gly Ala Gly Gly Arg Tyr
    290                 295                 300

Ile Cys Tyr Asp His Val Val Arg Arg Gly Glu Glu Phe Ala Glu Leu
305                 310                 315                 320

Gln Arg Gln Leu Gly Leu Pro Ile Thr Gly Val Ala Ala Ala Ser Arg
                325                 330                 335

Pro Gly Tyr Ser Asp Asp Gly Asp Val Gly Gly Asp Gly Arg Phe Ala
            340                 345                 350

Leu Cys Asn Gly Lys Leu Ala Arg Leu Val Ser Ser Arg Arg Arg Cys
        355                 360                 365

Thr Tyr Asp Val Tyr Tyr Pro Ala Ser Tyr Asp
    370                 375
```

<210> SEQ ID NO 7
<211> LENGTH: 6506
<212> TYPE: DNA
<213> ORGANISM: Oryza sativa
<220> FEATURE:
<223> OTHER INFORMATION: suppressor of NH1-mediated lesion formation 6
(Snl6) genomic DNA, cinnamoyl-CoA reductase-like family

<400> SEQUENCE: 7

| | |
|---|---|
| atgcgggcgg cgctgctgca tggccacggg ggcggggcgg cggcggcggc ggcggccggg | 60 |
| tggcgcccct cggccggcga cgcggacgtc aagcgcaccg cgggcggcga cggggggcgcg | 120 |
| gcggggccgc gcaccgtctg cgtcacgggc ggcatctcct tcgtcgggtt cgccgtcgtc | 180 |
| gaccgcctgc tccggcacgg ctacaccgtg cgcctcgccc tcgagaccca aggtcagctc | 240 |
| caaatccagc tcaccccac atcttttacc gtttacctgt tcgattacct cctttgcctt | 300 |
| gtttggctgt ttcgcttctg tgtcaccgac atgtgggccc cggtcgccac atgtatctca | 360 |
| aagccccggc cacttgtgcc aatacattcc acgtattttt attatttat atacctcggc | 420 |
| aaaaaaaaca aacatgaaaa aacaaaaacg ctcgtgccta gcatgacgta ccccttcgct | 480 |
| agttcgctgt atccaatttc tggactttat ctcgcagcag tagattttac ttctaccagc | 540 |
| ttattgagcc gatcagtctt ccaatccatc ttaattacca ctcgtttttg gacaaaaggc | 600 |
| aagcgacttc ccagcataaa ccaagcttag ttgctgttca agccggatta gcagatactc | 660 |
| tgcgtctcct cccgaagtgt tgttggggat ggaaccttgc cacctaccgc tgcactgcgg | 720 |
| gtttggtgtg ctacctgcag tccggtcacc atttcgtcac atctccatag accggttgct | 780 |
| agcttggagt agctaggaac tactacgctg catcttcccg tcagtagaat ttgctttcgt | 840 |
| tggataatgg cgtaacgctc tttgacggtg tatatccatt tgcgaataga gaccaaacta | 900 |
| aaaaaaaaaa tattggcata atgctctgct cgggctggtg ggtggtatgg cagccacttt | 960 |
| cctatgcaca gtgtgcatgt agccgtgaga gtatacctaa tgatgattgc ttttatgctt | 1020 |
| tggtgaatat aaccaactta attacctact tggaaatgac agaccgaaag aaacgtgcga | 1080 |
| aagctaaaga gaggaacata tacgtttatg tctaattcgc cacacacaag gaaaaacgga | 1140 |
| agaaaaaaac aaatgctaac aaggagtagg attgatggga ggtggtagct agactgaatt | 1200 |
| agtttaagac gtacgcaacc atctctatga tcgatcagcg ttgaacattt gactactcgt | 1260 |
| atatataaag ctaccgggcg tatgatttcc tcgtgtagta gttagttatt ctcgcattcg | 1320 |
| tttttttcctc gtgctatatg cacaatcttt ggatgcattc aaaacattct gattgtgact | 1380 |
| ttctccatat accaatgggc tcatgcttat ggcgtaacat taaacttttc gccggttttt | 1440 |
| attcttgttc tggtggtcag ccggtttctt ggaagagga aattgatcgt agtttcaaag | 1500 |
| tctcctatac gactcgtcca gttggggatg aaacaatcta caaatcaaac actagcagag | 1560 |
| acgtacgcag aatttttttt tccactggca gcaccatttt tctttgaccc gaggtagaaa | 1620 |
| tcttcaggtc taccacatca tgattagatt tcaaccaacc agtgctccaa ttcggatacc | 1680 |
| cattttaaca ttgcgccact aattagtcag ctttgtgttg cttagttgag ccatacttta | 1740 |
| cgcgttctga tccttcacat cagctaacaa atccaatcct tccctgaac caaaatcttt | 1800 |
| cagtactgct cccttcaatt ccctagcaag aaagcagaga accttcgac aaacaaatag | 1860 |
| tgttgatact aattataagt gggtgctgga cttctgatag cttcgtttca acagtctaca | 1920 |
| cccaagggcc attaggaaaa tttatctgat gatagcttag ctccaatctt aatctggaac | 1980 |

```
aacatgtctg gtccattagg cctccactgg aatagaggaa tatcacggga gttgaactaa    2040
ttcttgtgaa aatcctgtag aagtcatgcc tttatcttta tgctatcact accattctct    2100
aagtcatcgc ggataagaaa ccatgggcaa gaaaattttc agaatatcaa aaagataaaa    2160
tcctctctcc ggtttcccag ccagctacga atagttggaa acacacctgc tgcttggcta    2220
tgcttataat agtggaacat gattcatatt tctggttttc aaatggagtc aggtgagaag    2280
gatggaacga gattattgat aaagtaccgt tccaaaaacg ttcttatcct tatcggacaa    2340
ttatcaatga tagataacag aaagtaaaat cacacggcat catcgctatt attttattaa    2400
agcaacatgg cttcttttt tttgtgagta ttcatgcaac catcgtaatc ttgacgtgta    2460
ataatttggc ttattgctat ttgctacatc gcagaggacc tggacaagct gagggagatg    2520
gagatgttcg gcgaggacgg ccgggacggc gtgtggacgg tgatggcgaa cgtgacggac    2580
cccgagagcc tgcaccgggc gttcgacgga tgcgccggcg tgtttcacac ctcggcgttc    2640
gtggatccgg ggggcatgtc cggctacacg gtgagtgcac caaactcggt ccctaacctt    2700
aagatcctcg caactactac acctacctat gttatgtgtt ccctaatgct gtcacagaag    2760
tcactaagta agttagttat gtgttcccta atgctgtcat atagaagtca ctaaataagt    2820
taggttagta aaatatagaa aaaatcatgc aaacaaaaca gagtgaactt gaagagaatg    2880
gcggaaaaca gagtatatat gctccatcta acattctaac tcaaggcgca actgaacatc    2940
aaagattgat gttgaatgtt tggtgtacta aaaaagagc aatattattt atggtcgtta    3000
agaaggtatc aagaagtact acaatttac tagaagacac taaatttac aattaaaaaa    3060 agatacctcc tgatacacca taaaataact cgtaaaagga acattgcgat tttctttgtg    3120
gtgatgtggt ggggacccag taacagtctg aacttctgga aatcaagcaa ttaattgaca    3180
cataacggcg ttcgggaatt tttgaagcca atggacatag atcattttcg taattaatgg    3240
catgcacatc acagagcctc agacatctgg cccagagaaa tttgtacagt tgagctgtag    3300
agtttgcatc tacatgtaca tggccttttgg tactgcacgt ggaggcactc atgcctcaaa    3360
attcagaaag attttgtaag accgagtgac gagactctgt agttcgtgta ccacacgggg    3420
aagattctgc tcattcttgg cttctcctcc aagagacac caaatagttt atggtacccg    3480
ttatctagaa acgttgggcg ctgcggtgtc catcacagat gttaacggtt ataccttcca    3540
tggttactta aaaactgaga ccttgctgat tgtcgattcc attggtcgta cagtagtatc    3600
aagatttcaa aaatgacaaa ccagtactat tgactgatgt gaagagcggc agatgccata    3660
aaactagcct tatttcgagc agacttaata aaaaagggt ttatagaaaa aggctcaatc    3720
accaactcgt accttcaagg attatttgt ttacgagcca atgtcttgtt tgttgccaaa    3780
ggcagggtgg gagaggatct tgaggctgga cagtcctcct tgtcgccctt tcgttgacat    3840
tttgccaaac ctgaagtcct cctgatggga gcaggttgta actggtagtc ctgcctatgc    3900
agatggtctt gcacctatct gatccatgaa gtagagcttc cggagcacag cattggtggg    3960
cgcacgcctg tcaactccgt cacctaattc attgacagaa aatcgcttgt ccatagcagg    4020
ggaccgggtt tattatctga taagaacggg taatcaggta ggattagtat ctgagtgtga    4080
tgagagtccg cattgcagca agagttggac aatacaacca ccgaatccac ttcggttggg    4140
tacttccaag cagccgtcag aatcatgacg accttagtgt aaccaaggcg attaaagaac    4200
agagatgcca tccagttgcg tcctactctg caacaatata tactccctct cttttagatt    4260
tattaacata tatataaata taggcaatat tataaaatct tatattgtga aatgcacaat    4320
agagggagta tgctagtaat aggctttatt ttactgttct tgaataccctt tattttttt    4380
```

```
accattcttg ttccacacaa tataacctct ttttaatgga agaaatttgc tgcaatttgg    4440
aggaaatgaa ctggttcaat gaaaatcctg taaaatttat gcgtttcaaa gtagccctac    4500
gttcgatttt gctatatatt tgtcgacaaa ttttcccccta aaaatttaac agatgtaatt    4560
acagtacaat cgtagtgtaa ttacactata acttgcatgt aattacactg taactatagt    4620
gtaacttgta tgtaactttc aaaaatctct ccgtaatatg ttatttcgat aaaatggagg    4680
tcgtgggaac aaattctttc acatatgtgt gtactgatga ttgttttctt cctcaccaaa    4740
acaaatcttg taatagatct aacaattcaa aattatgtga aacttacata taagttacac    4800
tgtagttaca tgcaagttac agtgtaatta catatatgtt acagtgtaat tacattatga    4860
ttgtattata attacatctg tcaaatttt aggagaaaat ttgtcaacaa atgtataggt    4920
agtcccccct acgtttggta tctcaatcac actagtgttt atcatttatc tgcagtaaga    4980
gcctattgta gctaaaataa accttaccaa atttggtat tgccaaaatt ttggcaagat    5040
gacaatattg cgaaaatttt ggcaggatat cttatgtatt tacttaattt ggcaacaaac    5100
taaatataga tatttttta caactttaca ttaaaaaaat ggtatggttg aaaatagcat    5160
caaagtgaac gggcctgatt ttcgctagtg gaccgttcgc tctcacccat cattcctggt    5220
agtcaattct tgtgtagtca tggtaatttg ttgtttagta gcgattgggc gtacgattga    5280
ggcggtgtaa ttaacttttt ccctgttaat gtccaactct cgaacagaaa catatgcaa    5340 gcttggaggc gaaagcagca gagcaggtga tcgaggcgtg cgtgaggaca gagtccgtca    5400
gaaaatgcgt cttcacgtcg tcgttgctag catgtgtatg gaggcaaaat taccctcatg    5460
accgacggtt tcctaccatc atcgacgaga actgctggag cgatgagagc ttctgccgtg    5520
acaacaaggt gagtttgtta ctgtattaaa aaaaaaagga gggtttgttc agtgacacgg    5580
aagcgcactt gcaatggtgg atgcataagc atattttatc acccaccaac tgaatctttt    5640 tttttcttg tggaaaattt gtgcaatcta atgactttct ggataaactt ttcagctgtg    5700
gtttgcactg ggcaagacgg cagcggagaa gacggcgtgg agggcagcca ggggtaggga    5760
cctgaagctg gtcaccgtct gcccggcgct ggtcaccggt ccgggattcc gccgccgcaa    5820
ctccaccgcc tccatcgcct acctcaaagg tacactacag gcttcgatac gagcatgtaa    5880
actacgatcg gagaaaggaa catggtgtgc ctttgtgctt gtgcagtaca cactgacatg    5940
tcttgcgtgt cgacaggggc tcgcgccatg ctcgccgacg gcctgctcgc gacggcgagc    6000
gtggagacgg tggcggaggc gcacgtccgg gtgtacgagg cgatgggcga caacacggcc    6060
ggcgggaggt acatctgcta cgaccacgtg gtgaagaggc ccgaggagtt cgcggagctg    6120
gagcgccagc tggggatccc gcgcagagcg gcggcggcgg cggccgcgca ggactccggc    6180
gaccggccgg cgaggttcga tctgtgcagg cagaagctgg cgaggctcat gtccacccga    6240
aggcggtgca cgtacgacga ctactactcc gtcgcattcg actagatatc tagctaggct    6300
aggcaaactg gcgagcacca ccgtgcaatg gcttgcagca ctgcaccaat gatggatcat    6360
ctgggttggg ttttgcctga agggtgcaag aggacgaagt cgtagtggat ggatggaaga    6420
agagtgtgtg acatcatgta catagtgcga tcttgtaggc tgtttgatgc atcaataaag    6480
cttgatcgag ccccattttt tggcta                                        6506
```

<210> SEQ ID NO 8
<211> LENGTH: 4
<212> TYPE: PRT
<213> ORGANISM: Artificial Sequence
<220> FEATURE:

<223> OTHER INFORMATION: synthetic DEAD-box motif

<400> SEQUENCE: 8

Asp Glu Ala Asp
 1

<210> SEQ ID NO 9
<211> LENGTH: 19
<212> TYPE: DNA
<213> ORGANISM: Artificial Sequence
<220> FEATURE:
<223> OTHER INFORMATION: synthetic Xa21 genotyping forward primer H3
      frag F

<400> SEQUENCE: 9
atagcaactg attgcttgg                                                19

<210> SEQ ID NO 10
<211> LENGTH: 21
<212> TYPE: DNA
<213> ORGANISM: Artificial Sequence
<220> FEATURE:
<223> OTHER INFORMATION: synthetic Xa21 genotyping reverse primer 3'
      Xa21 R

<400> SEQUENCE: 10
cgatcggtat aacagcaaaa c                                             21

<210> SEQ ID NO 11
<211> LENGTH: 21
<212> TYPE: DNA
<213> ORGANISM: Artificial Sequence
<220> FEATURE:
<223> OTHER INFORMATION: synthetic NH1ox genotyping forward primer Ubi-1

<400> SEQUENCE: 11
tgatatactt ggatgatggc a                                             21

<210> SEQ ID NO 12
<211> LENGTH: 19
<212> TYPE: DNA
<213> ORGANISM: Artificial Sequence
<220> FEATURE:
<223> OTHER INFORMATION: synthetic NH1ox genotyping reverse primer
      PrNH22

<400> SEQUENCE: 12
ggacggcgat gcgcgcgtc                                                19

<210> SEQ ID NO 13
<211> LENGTH: 20
<212> TYPE: DNA
<213> ORGANISM: Artificial Sequence
<220> FEATURE:
<223> OTHER INFORMATION: synthetic Deletion 1A genotyping forward primer
      Os01g21420_F

<400> SEQUENCE: 13
agcaggaggg agaagacaca                                               20

<210> SEQ ID NO 14
<211> LENGTH: 20
<212> TYPE: DNA
<213> ORGANISM: Artificial Sequence
<220> FEATURE:
<223> OTHER INFORMATION: synthetic Deletion 1A genotyping reverse primer
      Os01g21420_R

<400> SEQUENCE: 14
accaggaagc aaagcaaaga                                          20

<210> SEQ ID NO 15
<211> LENGTH: 18
<212> TYPE: DNA
<213> ORGANISM: Artificial Sequence
<220> FEATURE:
<223> OTHER INFORMATION: synthetic Deletion 1B genotyping forward primer
      Os01g45160_F

<400> SEQUENCE: 15
gaagacgaac cgcgtctg                                            18

<210> SEQ ID NO 16
<211> LENGTH: 21
<212> TYPE: DNA
<213> ORGANISM: Artificial Sequence
<220> FEATURE:
<223> OTHER INFORMATION: synthetic Deletion 1B genotyping reverse primer
      Os01g45160_R

<400> SEQUENCE: 16
ggtgtcacct ctgatcacct g                                        21

<210> SEQ ID NO 17
<211> LENGTH: 20
<212> TYPE: DNA
<213> ORGANISM: Artificial Sequence
<220> FEATURE:
<223> OTHER INFORMATION: synthetic Deletion 2 genotyping forward primer
      Os02g33730_F

<400> SEQUENCE: 17
gttgcttgtt ggtgggaact                                          20

<210> SEQ ID NO 18
<211> LENGTH: 20
<212> TYPE: DNA
<213> ORGANISM: Artificial Sequence
<220> FEATURE:
<223> OTHER INFORMATION: synthetic Deletion 2 genotyping reverse primer
      Os02g33730_R

<400> SEQUENCE: 18
tccgtgggaa aatcaaagac                                          20

<210> SEQ ID NO 19
<211> LENGTH: 20
<212> TYPE: DNA
<213> ORGANISM: Artificial Sequence
<220> FEATURE:
<223> OTHER INFORMATION: synthetic Deletion 3 genotyping forward primer
      Os03g56234_F

<400> SEQUENCE: 19
tcctcagcag cttaccacct                                          20

<210> SEQ ID NO 20
<211> LENGTH: 20
<212> TYPE: DNA
<213> ORGANISM: Artificial Sequence
<220> FEATURE:
<223> OTHER INFORMATION: synthetic Deletion 3 genotyping reverse primer
      Os03g56234_R

<400> SEQUENCE: 20
tgcgtcgaac aagacgatag                                               20

<210> SEQ ID NO 21
<211> LENGTH: 20
<212> TYPE: DNA
<213> ORGANISM: Artificial Sequence
<220> FEATURE:
<223> OTHER INFORMATION: synthetic Deletion 7 genotyping forward primer
      Os07g35810_F

<400> SEQUENCE: 21
tacaccggta atccgatggt                                               20

<210> SEQ ID NO 22
<211> LENGTH: 20
<212> TYPE: DNA
<213> ORGANISM: Artificial Sequence
<220> FEATURE:
<223> OTHER INFORMATION: synthetic Deletion 7 genotyping reverse primer
      Os07g35810_R

<400> SEQUENCE: 22
ggcccaagga ctaaggtctc                                               20

<210> SEQ ID NO 23
<211> LENGTH: 26
<212> TYPE: DNA
<213> ORGANISM: Artificial Sequence
<220> FEATURE:
<223> OTHER INFORMATION: synthetic PCR amplification primer for 425bp
      from the 3' end of LOC_Os01g45200

<400> SEQUENCE: 23
gaattcaggc ttcgatacga gcatgt                                        26

<210> SEQ ID NO 24
<211> LENGTH: 25
<212> TYPE: DNA
<213> ORGANISM: Artificial Sequence
<220> FEATURE:
<223> OTHER INFORMATION: synthetic PCR amplification primer for 425bp
      from the 3' end of LOC_Os01g45200

<400> SEQUENCE: 24
agatctgtcg aatgcgacgg agtag                                         25

<210> SEQ ID NO 25
<211> LENGTH: 23
<212> TYPE: DNA
<213> ORGANISM: Artificial Sequence
<220> FEATURE:
<223> OTHER INFORMATION: synthetic NH1 real-time quantitative RT-PCR
      forward primer NH1_RT_S2

<400> SEQUENCE: 25
caggtgagag tctacgagga agg                                           23

<210> SEQ ID NO 26
<211> LENGTH: 24
<212> TYPE: DNA
<213> ORGANISM: Artificial Sequence
<220> FEATURE:
<223> OTHER INFORMATION: synthetic NH1 real-time quantitative RT-PCR
      reverse primer NH1_RT_AS2

<400> SEQUENCE: 26
ttgtctttca ggaggtggat ttgc                                              24

<210> SEQ ID NO 27
<211> LENGTH: 24
<212> TYPE: DNA
<213> ORGANISM: Artificial Sequence
<220> FEATURE:
<223> OTHER INFORMATION: synthetic Os01g45190 real-time quantitative
      RT-PCR forward primer BB190_RT_S1

<400> SEQUENCE: 27
gctatcggtg acttcatcaa tatc                                              24

<210> SEQ ID NO 28
<211> LENGTH: 19
<212> TYPE: DNA
<213> ORGANISM: Artificial Sequence
<220> FEATURE:
<223> OTHER INFORMATION: synthetic Os01g45190 real-time quantitative
      RT-PCR reverse primer BB190_RT_AS1

<400> SEQUENCE: 28
agactctgcc aggtgttcc                                                    19

<210> SEQ ID NO 29
<211> LENGTH: 26
<212> TYPE: DNA
<213> ORGANISM: Artificial Sequence
<220> FEATURE:
<223> OTHER INFORMATION: synthetic Os01g45200 real-time quantitative
      RT-PCR forward primer 200_RNAi_F2

<400> SEQUENCE: 29
caccgtggac ggtgatggcg aacgtg                                            26

<210> SEQ ID NO 30
<211> LENGTH: 21
<212> TYPE: DNA
<213> ORGANISM: Artificial Sequence
<220> FEATURE:
<223> OTHER INFORMATION: synthetic Os01g45200 real-time quantitative
      RT-PCR reverse primer 200_cDNA_R2

<400> SEQUENCE: 30
gcaacgacga cgtgaagacg c                                                 21

<210> SEQ ID NO 31
<211> LENGTH: 20
<212> TYPE: DNA
<213> ORGANISM: Artificial Sequence
<220> FEATURE:
<223> OTHER INFORMATION: synthetic 03g18850 real-time quantitative
      RT-PCR forward primer

<400> SEQUENCE: 31
agttcctgga cgtggacaag                                                   20

<210> SEQ ID NO 32
<211> LENGTH: 20
<212> TYPE: DNA
<213> ORGANISM: Artificial Sequence
<220> FEATURE:
<223> OTHER INFORMATION: synthetic 03g18850 real-time quantitative
      RT-PCR reverse primer

<400> SEQUENCE: 32

```
tctcgtcctt cacctccact                                               20
```

<210> SEQ ID NO 33
<211> LENGTH: 20
<212> TYPE: DNA
<213> ORGANISM: Artificial Sequence
<220> FEATURE:
<223> OTHER INFORMATION: synthetic 12g36850 real-time quantitative
      RT-PCR forward primer

<400> SEQUENCE: 33

```
acgcagggag cgtatacaag                                               20
```

<210> SEQ ID NO 34
<211> LENGTH: 20
<212> TYPE: DNA
<213> ORGANISM: Artificial Sequence
<220> FEATURE:
<223> OTHER INFORMATION: synthetic 12g36850 real-time quantitative
      RT-PCR reverse primer

<400> SEQUENCE: 34

```
caccctgctc ttaacctcca                                               20
```

<210> SEQ ID NO 35
<211> LENGTH: 18
<212> TYPE: DNA
<213> ORGANISM: Artificial Sequence
<220> FEATURE:
<223> OTHER INFORMATION: synthetic 02g41650 real-time quantitative
      RT-PCR forward primer

<400> SEQUENCE: 35

```
ggcctccaca tcgctcgc                                                 18
```

<210> SEQ ID NO 36
<211> LENGTH: 16
<212> TYPE: DNA
<213> ORGANISM: Artificial Sequence
<220> FEATURE:
<223> OTHER INFORMATION: synthetic 02g41650 real-time quantitative
      RT-PCR reverse primer

<400> SEQUENCE: 36

```
acggcctcgc ggtcga                                                   16
```

<210> SEQ ID NO 37
<211> LENGTH: 20
<212> TYPE: DNA
<213> ORGANISM: Artificial Sequence
<220> FEATURE:
<223> OTHER INFORMATION: synthetic ubiquitin real-time quantitative
      RT-PCR forward primer UBQ5_F

<400> SEQUENCE: 37

```
atggccaacc acttcgaccg                                               20
```

<210> SEQ ID NO 38
<211> LENGTH: 22
<212> TYPE: DNA

```
<213> ORGANISM: Artificial Sequence
<220> FEATURE:
<223> OTHER INFORMATION: synthetic ubiquitin real-time quantitative
      RT-PCR reverse primer UBQ5_R

<400> SEQUENCE: 38
taagcctgct ggttgtagac gt                                              22
```

INHIBITION OF SNL6 EXPRESSION FOR BIOFUEL PRODUCTION

CROSS-REFERENCED TO RELATED APPLICATIONS

This application is the U.S. national stage entry of International application no. PCT/US2011/040941, filed Jun. 17, 2011, which claims benefit of U.S. provisional application No. 61/356,503, filed Jun. 18, 2010, each application is incorporated by reference for all purposes.

STATEMENT AS TO RIGHTS TO INVENTIONS MADE UNDER FEDERALLY SPONSORED RESEARCH AND DEVELOPMENT

This invention was made with government support under DE-AC02-05CH11231 awarded by the United States Department of Energy. The government has certain rights in the invention.

REFERENCE TO SUBMISSION OF A SEQUENCE LISTING

The Sequence Listing written in file SEQTXT_77429-858450-008310US.txt, created on Dec. 14, 2012, 33,309 bytes, machine format IBM-PC, MS-Windows operating system, is hereby incorporated by reference.

BACKGROUND OF THE INVENTION

Biofuel production from plant biomass is increasingly being touted as a solution for the worldwide need for renewable energy. Biofuel from plant biomass is produced by extracting soluble sugars from the plant biomass and fermenting the sugars into ethanol. Most plant biomass, however, is cellulosic biomass, which can be difficult to break down into sugars due to the presence of lignin and the complex structure of cell walls.

Lignin is a complex, heterogeneous phenolic polymer that binds with cellulose to form cell walls. Lignin is deposited in cell walls during plant development and provides structure, support, and imperviousness to the cell walls. Additionally, lignin is deposited during defense responses to create a barrier against infection of pathogens, as most pathogens are unable to degrade lignin.

Because the presence of lignin hinders the extraction of soluble sugars from plant biomass, it has been proposed that sugar extractability can be increased by decreasing the amount of lignin in a plant. Indeed, previous reports have confirmed that there is a correlation between decreased lignin content and increased sugar extractability [43]. However, decreasing lignin content in a plant can lead to a variety of defects in the plant, such as decreased plant size, limp plants that cannot stay upright, and plants that are more susceptible to pathogens. These defects make the plants less suitable for use in biofuel production.

Therefore, there is a need in the field for methods of increasing the extractability of soluble sugars in a plant that do not result in morphological or developmental defects such as plant height, tiller number, or general appearance. The present invention satisfies this need and others.

BRIEF SUMMARY OF THE INVENTION

The invention provides, in part, plants that have been engineered to have inhibited endogenous expression of an Snl6 gene, methods of engineering such plants, and methods of using such plants, e.g., to obtain an increased amount of soluble sugar for biofuel production. Thus, in one aspect, the invention provides a plant in which an endogenous Snl6 gene is functionally disrupted, e.g., by knocking out the gene or otherwise mutagenizing the gene to inactivate or reduce expression, e.g., to less than 80% of the level of expression, typically less than 50% of the level of expression, more typically to less than 20%, or less than 10% of the level of expression in a corresponding wildtype plant in which the Snl6 gene is not functionally disrupted. In some embodiments, the endogenous Snl6 gene is deleted. In some embodiments, the endogenous Snl6 gene is inactivated by insertional mutagenesis. In some embodiments, the promoter of the Snl6 gene is disrupted, e.g., by mutagenesis, so that Snl6 expression is reduced, e.g., to less than 80%, less than 70%, or less than 60% of the level of expression, typically less than 50% of the level of expression, more typically to less than 20%, or less than 10% of the level of expression in a corresponding wildtype plant in which the promoter of the Snl6 gene is not functionally disrupted.

In a further aspect, the invention provides a plant that comprises a recombinant expression cassette that encodes a polynucleotide that hybridizes to a Snl6 gene and inhibits expression of the Snl6 gene. In one embodiment, the plant comprises a recombinant expression vector that encodes a polynucleotide, wherein the polynucleotide is at least 60% identical, at least 65%, at least 70%, at least 75%, at least 80%, at least 85%, at least 90%, or at least 95% identical, to at least 100 or at least 200 contiguous nucleotides of a nucleic acid sequence of SEQ ID NO:1 or SEQ ID NO:7; or is at least 60% identical, at least 65%, at least 70%, at least 75%, at least 80%, at least 85%, at least 90%, or at least 95% identical, to at least 100 or at least 200 contiguous nucleotides of a nucleic acid sequence encoding any one of SEQ ID NOs:2-6 or a complement thereof.

In some embodiments, the polynucleotide comprises a sequence that is at least 90% identical to 20 contiguous nucleotides, or at least 30, 40, 50, 100, or at least 200 contiguous nucleotides, of a nucleic acid sequence of SEQ ID NO:1 or SEQ ID NO:7, or a complement thereof; or is at least 90% identical to 20 contiguous nucleotides, or at least 30, at least 40, at least 50, at least 100, or at least 200 contiguous nucleotides to a nucleic acid sequence encoding any of SEQ ID NOs:2-6, or a complement thereof. In some embodiments, the polynucleotide encodes an siRNA, an antisense polynucleotide, a microRNA, or a sense suppression nucleic acid.

In some embodiments, the plant has at least a 10% increase, and in some embodiments, at least a 20% or at least a 50% or more, in sugar extractability compared to the control plant lacking the vector. In some embodiments, the plant does not exhibit developmental defects. In some embodiments, the plant that is engineered in accordance with the invention is selected from the group consisting of rice, corn, switchgrass, sorghum, millet, miscanthus, sugarcane, poplar, pine, alfalfa, eucalyptus, wheat, soy, cotton, barley, turfgrass, tobacco, hemp, potato, bamboo, rape, sugar beet, sunflower, willow, and *Brachypodium*. In some embodiments, the plant is rice.

In some embodiments, the invention provides a plant cell from a plant that is engineered to inhibit endogenous expression of a Snl6 gene. In some embodiments, the invention provides a seed, flower, leaf, stem, stalk, fruit, or processed food from such plants.

In another aspect, the invention provides a method of improving the amount of soluble sugar obtained from plant biomass material, the method comprising providing plant biomass material from any plant as described herein above that has decreased Snl6 expression; performing a saccharification reaction; and obtaining soluble sugar. In some embodiments, the Snl6 gene is deleted or knocked out in the plant. In some embodiments, the plant comprises a recombinant expression vector the encodes a nucleic acid that inhibits Snl6 gene expression. In some embodiments, the amount of sugar extractable from the plant biomass material is increased by at least 10%, or at least 20%, or at least 50%, or more, compared to the amount of sugar extractable from plant biomass material from the wild-type plant.

In yet another aspect, the invention provides a saccharification reaction comprising plant biomass material from such engineered plants.

In a further aspect, the invention provides a method of obtaining an increased amount of soluble sugars from a plant in a saccharification reaction, the method comprising inhibiting the expression of an endogenous Snl6 gene in the plant, using plant material in a saccharification reaction, thereby increasing the amount of extracted sugar compared to a wild-type plant in which expression of the endogenous gene has not been inhibited.

In some embodiments, the inhibiting step comprises introducing into the plant an expression cassette that encodes a polynucleotide that hybridizes to an endogenous snl6 gene and inhibits expression In some embodiments, the polynucleotide is at least 70% identical to at least 100 or at least 200 contiguous nucleotides of a nucleic acid sequence of SEQ ID NO:1 or SEQ ID NO:7, or a complement thereof, or is at least 70% identical to at least 100 or at least 200 contiguous nucleotides of a nucleic acid sequence encoding any of SEQ ID NOs:2-6 or a complement thereof. In some embodiments, the polynucleotide comprises a sequence that is at least 90% identical to at least 50, or at least 100, or at least 200 contiguous nucleotides to a nucleic acid sequence of SEQ ID NO:1 or SEQ ID NO:7 or a complement thereof; or is at least 90% identical to at least 50, or at least 100, or at least 200 contiguous nucleotides of a nucleic acid sequence encoding any of SEQ ID NOs:2-6 or a complement thereof. In some embodiments, the polynucleotide encodes an siRNA, an antisense polynucleotide, a microRNA, or a sense suppression nucleic acid.

In some embodiments, the plant that is used in accordance with this method is selected from the group consisting of rice, corn, switchgrass, sorghum, millet, miscanthus, sugarcane, poplar, pine, alfalfa, eucalyptus, wheat, soy, cotton, barley, turfgrass, tobacco, hemp, potato, bamboo, rape, sugar beet, sunflower, willow, and Brachypodium. In some embodiments, the plant is rice.

In yet another aspect, the invention provides a method of improving the amount of soluble sugar obtained from plant biomass material, the method comprising providing plant biomass material from a plant in which endogenous Snl6 gene expression is inhibited; performing a saccharification reaction; and obtaining soluble sugar. In some embodiments, the amount of sugar extractable from the plant biomass material is increased by at least 10% compared to the amount of sugar extractable from plant biomass material from the wild-type plant.

In a further aspect, the invention provides a method of decreasing the lignin content of a plant, the method comprising decreasing expression of an endogenous Snl6 gene. Decreased expression of the endogenous Snl6 gene can be achieved using any method. Preferably, a plant of the invention is genetically manipulated to decrease expression of the endogenous Snl6 gene to reduce the lignin content.

The lignin content of such a plant of the invention is often reduced by at least 10%, or at least 20%, at least 30%, at least 40% at least 50%, or more, e.g., at least 60 or 70%, compared to a corresponding plant that has not been manipulated to decrease Snl6 expression.

In another aspect, the invention provides bulk harvested material comprising material from at least two engineered plants that have decreased expression of an endogenous Snl6 gene as described herein. In some embodiments, the at least two engineered plants are selected from the group consisting of rice, corn, switchgrass, sorghum, millet, miscanthus, sugarcane, poplar, pine, alfalfa, eucalyptus, wheat, soy, cotton, barley, turfgrass, tobacco, hemp, potato, bamboo, rape, sugar beet, sunflower, willow, and Brachypodium.

BRIEF DESCRIPTION OF THE DRAWINGS

FIG. 14. Complete list of deleted genes in snl6-FN. DEAD=SEQ ID NO:8.

FIG. 15. Protein alignment for rice Snl6 and closely related homologs. The protein sequence for rice Snl6 (SEQ ID NO:2) was aligned to the protein sequences of Snl6 homologs in sorghum (SEQ ID NO:3), maize (SEQ ID NO:4), *Brachypodium* (SEQ ID NO:5), and rice Os05g50250 (SEQ ID NO:6).

DETAILED DESCRIPTION OF THE INVENTION

Definitions

Figure 1:
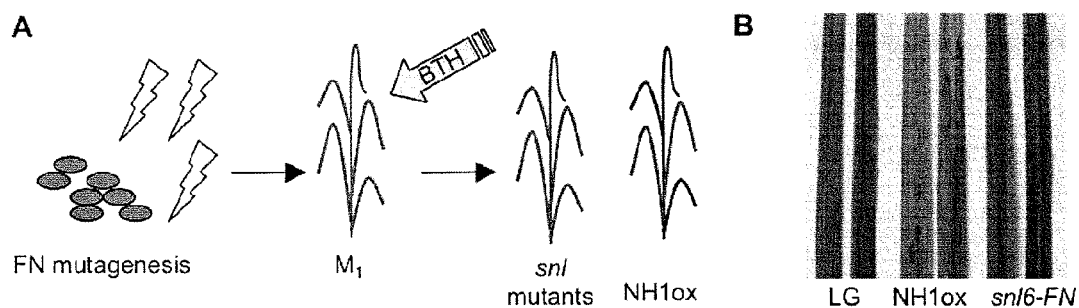
FIG. 1. Identification of the snl6-FN mutant. (A) Cartoon of mutant screen used to identify suppressors of BTH-induced, NH1-mediated lesion mimic (snl) mutants. NH1ox seeds were treated with Fast Neutron (FN) mutagenesis ($M_1$). $M_2$ plants were treated with BTH and then screened for the appearance of the lesion mimic phenotype. snl6-FN (line 11-3) did not develop lesions after BTH treatment. (B) 8-week old plants were treated with BTH. Plants were assessed for the presence of the lesion mimic phenotype. Image was taken two weeks after BTH treatment. LG, NH1ox and snl6-FN (line: 11-3-2) were compared.

The term "Snl6 gene," in the context of this invention, refers to a nucleic acid that encodes a suppressor of NH1-mediated lesion formation (Snl) protein, or fragment thereof. As described herein, Snl6 is a member of the cinnamoyl-CoA reductase-like gene family. In some embodiments, an Snl6 gene or Snl6 nucleic acid comprises the nucleic acid sequence of SEQ ID NO:1 or SEQ ID NO:7 or a fragment thereof, or is substantially identical to SEQ ID NO:1 or SEQ ID NO:7 or a fragment thereof. Thus, a Snl6 gene can, for example, (1) have at least 70% identity, 75% identity, 80% identity, 85% identity, 90% identity, at least 95% or greater, identity to SEQ ID NO:1 or SEQ ID NO:7 or a fragment thereof over a comparison window of at least 200, 250, 300, 350, 400, 450, or more nucleotides; or (2) comprise at least 200, 250, 300, 350, 400, 450, or more, contiguous nucleotides of SEQ ID NO:1 or SEQ ID NO:7.

An "Snl6 polypeptide" is an amino acid sequence encoded by an Snl6 nucleic acid. In some embodiments, an Snl6 polypeptide comprises the amino acid sequence of SEQ ID NO:2, SEQ ID NO:3, SEQ ID NO:4, SEQ ID NO:5, or SEQ ID NO:6 or is substantially identical to SEQ ID NO:2, SEQ ID NO:3, SEQ ID NO:4, SEQ ID NO:5, or SEQ ID NO:6 or a fragment or domain thereof that has Snl6 activity.

As used herein, a "homolog" or "ortholog" of an Snl6 gene is a second gene in the same plant type or in a different plant type that is substantially identical (determined as described below) to a sequence in a first gene.

The terms "nucleic acid" and "polynucleotide" are used interchangeably and refer to a single or double-stranded polymer of deoxyribonucleotide or ribonucleotide bases read from the 5' to the 3' end. A nucleic acid of the present invention will generally contain phosphodiester bonds, although in some cases, nucleic acid analogs may be used that may have alternate backbones, comprising, e.g., phosphoramidate, phosphorothioate, phosphorodithioate, or O-methylphophoroamidite linkages (see Eckstein, Oligonucleotides and Analogues: A Practical Approach, Oxford University Press); positive backbones; non-ionic backbones, and non-ribose backbones. Thus, nucleic acids or polynucleotides may also include modified nucleotides that permit correct read-through by a polymerase. "Polynucleotide sequence" or "nucleic acid sequence" includes both the sense and antisense strands of a nucleic acid as either individual single strands or in a duplex. As will be appreciated by those in the art, the depiction of a single strand also defines the sequence of the complementary strand; thus the sequences described herein also provide the complement of the sequence. Unless otherwise indicated, a particular nucleic acid sequence also implicitly encompasses variants thereof (e.g., degenerate codon substitutions) and complementary sequences, as well as the sequence explicitly indicated. The nucleic acid may be DNA, both genomic and cDNA, RNA or a hybrid, where the nucleic acid may contain combinations of deoxyribo- and ribo-nucleotides, and combinations of bases, including uracil, adenine, thymine, cytosine, guanine, inosine, xanthine hypoxanthine, isocytosine, isoguanine, etc.

The terms "decreased expression," "reduced expression," or "inhibited expression" of an endogenous Snl6 gene refer interchangeably to a reduction in the level of expression of the Snl6 gene in an engineered plant in which Snl6 gene expression has been disrupted compared to the level of expression in a wild-type plant in which Snl6 expression has not been disrupted. Thus, decreased expression can be a reduction in expression of an Snl6 gene of 10%, 20%, 30%, 40%, 50%, 60%, 70%, 80%, or 90% or greater. Decreased expression can be assessed by measuring decreases in the level of RNA encoded by the gene and/or decreases in the level of Snl6 protein or protein activity. Snl6 protein/protein activity can be assessed directly or indirectly, e.g., by measuring an endpoint such as amount of sugar extractable from a plant in which a Snl6 gene is inhibited, or by measuring the amount of phenolics synthesized in a plant in which a Snl6 gene is inhibited, and/or by assessing the lignin content of a plant in which a Snl6 gene expression is inhibited.

In the context of this invention, the phrase "functionally inactive" with regard to an endogenous Snl6 gene means that the Snl6 gene is deleted or otherwise mutated or inhibited, such that expression of the gene does not occur, or occurs at a low level, e.g., at a level of less than 20% or less than 10% compared to a corresponding in plant in which the Snl6 gene is not deleted or otherwise mutated or inhibited.

The phrase "absence of developmental defects" or "does not exhibit developmental defects," as used herein, refers to the absence of phenotypic defects that are frequently observable in a plant having inhibited gene and/or protein expression as compared to a wild-type plant. As used herein, the absence of developmental defects can be determined by assessing for the presence or absence of morphological differences in the plant having inhibited Snl6 gene and/or protein expression, such as substantially reduced height of the plant, absence of a plant part, substantially reduced tiller number, or substantially reduced panicle weight. For example, a plant that does not exhibit developmental defects will have a plant height that is not substantially reduced as compared to a wild-type plant (i.e., a height that is at least 75% of the height of the wild-type plant, at least 80%, 85%, 90%, 95%, or greater), a tiller number that is not substantially reduced as compared to a wild-type plant (i.e., a tiller number that is at least 75% of the tiller number of the wild-type plant, at least 80%, 85%, 90%, 95%, or greater); and a panicle weight that is not substantially reduced as compared to a wild-type plant (i.e., a panicle weight that is at least 75% of the panicle weight of the wild-type plant, at least 80%, 85%, 90%, 95%, or greater).

The phrase "substantially identical," in the context of two nucleic acids or polypeptides, refers to a sequence or subsequence that has at least 50% identity, typically at least 60% sequence identity, to a reference sequence. Percent identity can be any integer from 50% to 100%. In some embodiments, a sequence is at least 60%, 65%, 70%, 75%, 80%, 85%, 90%, 91%, 92%, 93%, 94%, 95%, 96%, 97%, 98%, or 99% identical when compared to a reference sequence. For example, an Snl6 polypeptide may have a sequence that is at least 60%, 65%, 70%, 75%, 80%, 85%, 90%, 91%, 92%, 93%, 94%, 95%, 96%, 97%, 98%, or 99% identical to a sequence of SEQ ID NO:2, SEQ ID NO:3, SEQ ID NO:4, SEQ ID NO:5, or SEQ ID NO:6.

In the case of inhibition of endogenous genes (e.g., by antisense, or sense suppression) one of skill will recognize that the introduced polynucleotide sequence need not be perfectly identical and may be "substantially identical" to a sequence of the gene from which it was derived. One of skill will also recognize that for inhibition of endogenous genes, the introduced sequence need not be perfectly identical to a sequence of the target endogenous gene. The introduced polynucleotide sequence will typically be at least substantially identical (as determined below) to the target endogenous sequence. Thus, an introduced "polynucleotide sequence from" an Snl6 gene may not be identical to the target Snl6 gene to be suppressed, but is functional in that it is capable of inhibiting expression of the target Snl6 gene.

Two nucleic acid sequences or polypeptides are said to be "identical" if the sequence of nucleotides or amino acid residues, respectively, in the two sequences is the same when aligned for maximum correspondence as described below. The term "complementary to" is used herein to mean that the sequence is complementary to all or a portion of a reference polynucleotide sequence.

Optimal alignment of sequences for comparison may be conducted by the local homology algorithm of Smith and Waterman Add. *APL. Math.* 2:482 (1981), by the homology alignment algorithm of Needleman and Wunsch, *J. Mol. Biol.* 48:443 (1970), by the search for similarity method of Pearson and Lipman, *Proc. Natl. Acad. Sci.* (U.S.A.) 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection. In some embodiments, percent identity is determined using the BLAST2 algorithm set at the default settings.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. A "comparison window" may be, e.g., 20, 50, 100, 400, or more nucleotides ore amino acids in length; or may be the entire length of the sequences being compared.

Proteins that are substantially identical include those that have conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, aspartic acid-glutamic acid, and asparagine-glutamine.

Another indication that nucleotide sequences are substantially identical is if two molecules hybridize to each other, or a third nucleic acid, under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is about 0.02 molar at pH 7 and the temperature is at least about 60° C. For example, stringent conditions for hybridization, such as RNA-DNA hybridizations in a blotting technique are those which include at least one wash in 0.2×SSC at 55° C. for 20 minutes, or equivalent conditions.

The term "recombinant," when used in reference to, e.g., a cell or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "expression vector" refers to a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The term "biomass," as used herein, refers to plant material that is processed to provide a product, e.g., a biofuel such as ethanol, or livestock feed. Such plant material can include whole plants, or parts of plants, e.g., stems, leaves, branches, shoots, roots, tubers, and the like.

The term "plant," as used herein, refers to whole plants, shoot vegetative organs and/or structures (e.g., leaves, stems and tubers), branches, roots, flowers and floral organs (e.g., bracts, sepals, petals, stamens, carpels, anthers), ovules (including egg and central cells), seed (including zygote, embryo, endosperm, and seed coat), fruit (e.g., the mature ovary), seedlings, and plant tissue (e.g., vascular tissue, ground tissue, and the like). The term also encompasses individual plant cells, groups of plant cells (e.g., cultured plant cells), protoplasts, plant extracts, seeds, and progeny thereof. The term includes plants of a variety of a ploidy levels, including polyploid, diploid and haploid.

The term "progeny" refers generally to the offspring of a cross, and includes direct F1 progeny, as well as later generations of F2, F3, etc.

The terms "saccharification" or "saccharification reaction" refer to a process of converting biomass, usually cellulosic or lignocellulosic biomass, into monomeric sugars, such as glucose and xylose. "Soluble sugar" refers to the monomeric sugar that is produced from the saccharification of biomass.

The term "improving the amount" or "improved amount," when referring to an amount of sugar or soluble sugar obtained from a plant of the present invention, refers to an increase in the amount or yield of sugar that is obtained from saccharification of biomass per amount of starting material, in comparison to corresponding biomass from a wild-type plant. In the context of the present invention, "corresponding biomass from a wild-type plant" refers to plant material that is from the same part of the plant as the biomass from a plant having inhibited expression of an endogenous Snl6 gene. As understood in the art, improved amount or improved yield is based upon comparisons of the same amount of corresponding plant material. As used herein, "increasing sugar extractability" refers to the ability to increase the yield of sugar from saccharification of biomass per amount of starting material.

The term "bulk harvested material" refers to combined plant material harvested from at least two plants, preferably at least 5, 10, 25, 50, 100, 500, or 1000 or more plants. The plant material may be whole plants, or parts of the plants, e.g., leaves or stems harvested from the plants. In some embodiments, the plant material present in the bulk harvested material is crushed or milled to a desired particle size, e.g., a size that is useful for producing biofuel.

Introduction

This invention is based, in part, on the surprising discovery that the inhibition of the gene Snl6 in plants results in increased sugar extractability, an important trait for the production of cellulosic biofuels, while not resulting in an obvious morphologic phenotype as compared to a plant in which Snl6 expression has not been inhibited. Snl6 is annotated as a cinnamoyl-CoA reductase (CCR)-like gene. However, Snl6 is not closed related by sequence to previously characterized CCR genes such as rice CCR1 and *Arabidopsis* CCR1 and CCR2. CCRs exist as multi-gene families with at least 7 and 14 annotated members in *Arabidopsis* and rice, respectively. Although several studies have shown that CCR is involved in lignin biosynthesis, the exact role of CCR in lignin biosynthesis is not clear. Moreover, studies from *Arabidopsis* and tobacco indicate that down-regulation of CCR result in severe developmental phenotypes, including collapsed xylem cells, dwarfism, decrease in total lignin, a higher S/G ratio (syringyl-like lignin structures to guaiacyl-like lignin structures) in the lignin polymer, and the appearance of feruloyl tyramines. Within the CCR family, there is also a large amount of sequence variability, which appears to result in functional redundancy between CCRs in at least some cases.

In the present invention, inhibition of Snl6 in a plant results in decreased synthesis of phenolics in the plant and decreased lignin content but does not result in developmental defects such as dwarfism and other defects observed in CCR downregulation. Therefore, plants of the present invention or bulk harvested material from such plants, are suitable for use in a saccharification reaction to obtain an increased amount of soluble sugar than can be obtained from wild-type plants.

In some embodiments, endogenous Snl6 expression is inhibited in a plant, such as a plant that is suitable for biomass energy, and the plant, or biomass material (e.g., stems, leaves, branches, shoots, roots, tubers, and the like) or bulk harvested material from the plant is used in a saccharification reaction to obtain an increased amount of soluble sugar, which can be used for biofuel production.

The present invention also provides methods of obtaining an increased amount of soluble sugars from a plant, or from biomass material or bulk harvested material from the plant, by inhibiting endogenous Snl6 expression in the plant. In some embodiments, the amount of soluble sugar that can be extracted from the plant is at least 10% more than what can be extracted from a wild-type plant in which Snl6 expression has not been inhibited.

Plants in which Snl6 Expression can be Inhibited

Snl6 expression can be inhibited as described herein in various kinds of plants. The plant may be a monocotyledonous plant or a dicotyledonous plant. In some embodiments of the invention, plants are green field plants.

In some embodiments, the plants are grown specifically for "biomass energy." For example, suitable plants include but are not limited to rice, corn, switchgrass, sorghum, millet, miscanthus, sugarcane, poplar, pine, alfalfa, eucalyptus, wheat, soy, cotton, barley, turfgrass, tobacco, hemp, potato, bamboo, rape, sugar beet, sunflower, willow, and *Brachypodium*.

Inhibition of Snl6 Expression

The invention employs various routine recombinant nucleic acid techniques. Generally, the nomenclature and the laboratory procedures in recombinant DNA technology described below are those well known and commonly employed in the art. Many manuals that provide direction for performing recombinant DNA manipulations are available, e.g., Sambrook & Russell, Molecular Cloning, A Laboratory Manual (3rd Ed, 2001); and Current Protocols in Molecular Biology (Ausubel et al., eds., 1994-1999, updated through 2008).

A. Snl6 Nucleic Acids and Proteins

Figure 11:
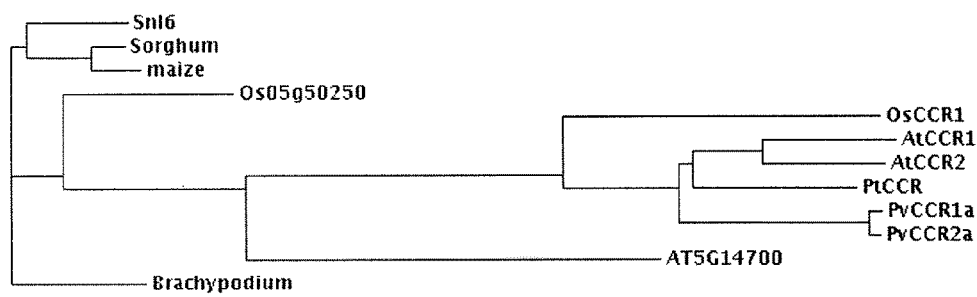
FIG. 11. Protein alignment for Snl6 and its homologs from other species. Close homologs were collected from NCBI (maize: ACR34585.1; Sorghum: EES03334.1), The *Brachypodium* Sequence Resource (JGI) (2g44800.1), TAIR (*Arabidopsis*: AT5G14700) and TIGR (rice: Os05g50250). Previously described CCRs were found through literature searches and sequences collected in NCBI as follows: *Arabidopsis* (AtCCR1: NP_173047; AtCCR2: NP_178197), poplar (PtCCR: AJ224986), switchgrass (PvCCR1a: GQ450296; PvCCR2a: GQ450301), and rice (OsCCR1). All sequences were compared using ClustalW2 web-based software.

Snl6 is a member of the cinnamoyl-CoA reductase (CCR)-like gene family, although it is more distantly related to previously characterized CCR genes. CCR genes have been identified in a variety of plants, such as rice, *Arabidopsis*, ryegrass, switchgrass, tobacco, and poplar. The CCR-like gene family has a large amount of sequence variability; for example, and as shown in FIG. 11, rice Snl6 (SEQ ID NO:2) is closely related to protein sequences in sorghum (SEQ ID NO:3), maize (SEQ ID NO:4), *Brachypodium* (SEQ ID NO:5), and rice (SEQ ID NO:6), and is more distantly related to several previously described CCRs, For example, Snl6 has 44% homology to *Arabidopsis* AT5G14700; 28% homology to rice OsCCR1; 28% homology to *Arabidopsis* ATCCR2 (NCBI Accession Number NP_178197); 28% homology to poplar PtCCR (NCBI Accession Number AJ224986); 27% homology to switchgrass PvCCR1a (NCBI Accession Number GQ450296); 27% homology to switchgrass PvCCR2a (NCBI Accession Number GQ450301); and 25% homology to *Arabidopsis* AtCCR1 (NCBI Accession Number NP_173047).

An Snl6 nucleic acid that is targeted for inhibition in the present invention encodes a protein that is substantially identical to SEQ ID NO:2. "Substantially identical," as used herein, refers to a sequence or subsequence that has at least 50% identity, typically at least 60% sequence identity or at least 70% sequence identity or higher, to a reference sequence. A comparison of protein sequences for Snl6 in rice (SEQ ID NO:2) and Snl6 homologs in sorghum (SEQ ID NO:3), maize (SEQ ID NO:4), *Brachypodium* (SEQ ID NO:5), and rice (SEQ ID NO:6) is provided in FIG. 15. As shown in FIG. 15, the protein sequences are highly conserved among rice Snl6 and its homologs. For example, the sorghum Snl6 homolog (SEQ ID NO:3) exhibits 86% identity to rice Snl6 (SEQ ID NO:2); the maize Snl6 homolog (SEQ ID NO:4) exhibits 82% identity to rice Snl6 (SEQ ID NO:2); the *Brachypodium* Snl6 homolog (SEQ ID NO:5) exhibits 81% identity to rice Snl6 (SEQ ID NO:2); and the rice Snl6 homolog (SEQ ID NO:6) exhibits 73% identity to rice Snl6 (SEQ ID NO:2).

Thus, in some embodiments, an Snl6 nucleic acid that is targeted for inhibition in the present invention encodes a polypeptide comprising a sequence that is at least 70% identical, at least 75%, 80%, 85%, 90%, 91%, 92%, 93%, 94%, 95%, 96%, 97%, 98%, or at least 99% identical to an amino acid of any of SEQ ID NOs:2-6 or a fragment thereof. In some embodiments, an Snl6 nucleic acid that is targeted for inhibition is at least 70% identical, at least 75%, 80%, 85%, 90%, 91%, 92%, 93%, 94%, 95%, 96%, 97%, 98%, or 99% identical to at least 100 contiguous nucleotides, or at least 200 contiguous nucleotides, of a nucleic acid sequence encoding any of SEQ ID NOs:2-6. Nucleic acids encoding SEQ ID NOs3, 4, 5, and 6 are known in the art and are available through the accession numbers listed in the description of FIG. 11.

In some embodiments, an Snl6 nucleic acid that is targeted for inhibition in the present invention comprises a sequence having at least 70%, at least 75%, 80%, 85%, 90%, 91%, 92%, 93%, 94%, 95%, 96%, 97%, 98%, or 99% identical to a nucleic acid sequence of SEQ ID NOs:1 or 7, or a fragment thereof. In some embodiments, an Snl6 nucleic acid that is targeted for inhibition is at least 70% identical, at least 75%, 80%, 85%, 90%, 91%, 92%, 93%, 94%, 95%, 96%, 97%, 98%, or 99% identical to at least 200 contiguous nucleotides of a nucleic acid sequence of SEQ ID NO:1 or SEQ ID NO:7.

B. Methods of Inhibiting Snl6 Expression

The invention provides methods of improving the amount of soluble sugar extractable from a plant, plant biomass material, or bulk harvested material from a plant by inhibiting expression of a nucleic acid molecule encoding Snl6. Endogenous expression of the Snl6 gene can be inhibited using any number of techniques well known in the art, such as antisense, siRNA, microRNA, dsRNA, sense suppression, or mutagenesis.

In some embodiments, Snl6 expression is inhibited by an antisense polynucleotide. In antisense technology, a nucleic acid segment from the desired gene is cloned and operably linked to a promoter such that the antisense strand of RNA will be transcribed. The expression cassette is then transformed into plants and the antisense strand of RNA is produced. In plant cells, it has been suggested that antisense RNA inhibits gene expression by preventing the accumulation of mRNA which encodes the enzyme of interest, see, e.g., Sheehy et al., *Proc. Nat. Acad. Sci. USA*, 85:8805-8809 (1988); Pnueli et al., *The Plant Cell* 6:175-186 (1994); and Hiatt et al., U.S. Pat. No. 4,801,340.

The antisense nucleic acid sequence transformed into plants will be substantially identical to at least a portion of the endogenous gene or genes to be repressed. The sequence, however, does not have to be perfectly identical to inhibit expression. Thus, an antisense or sense nucleic acid molecule encoding only a portion of an Snl6-encoding sequence can be useful for producing a plant in which Snl6 expression is suppressed. The vectors of the present invention can be designed such that the inhibitory effect applies to other proteins within a family of genes exhibiting homology or substantial homology to the target gene.

For antisense suppression, the introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments may be equally effective. In some embodiments, a sequence of at least, e.g., 20, 25, 30, 50, 100, 200, or more continuous nucleotides (up to mRNA full length) substantially identical to an endogenous Snl6 mRNA, or a complement thereof, can be used.

Catalytic RNA molecules or ribozymes can also be used to inhibit expression of an Snl6 gene. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs.

A number of classes of ribozymes have been identified. One class of ribozymes is derived from a number of small circular RNAs that are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, *solanum nodiflorum* mottle virus and subterranean clover mottle virus. The design and use of target RNA-specific ribozymes is described in Haseloff et al. *Nature,* 334:585-591 (1988).

Another method by which Snl6 expression can be inhibited is by sense suppression (also known as co-suppression). Introduction of expression cassettes in which a nucleic acid is configured in the sense orientation with respect to the promoter has been shown to be an effective means by which to block the transcription of target genes. For an example of the use of this method to modulate expression of endogenous genes see, Napoli et al., *The Plant Cell* 2:279-289 (1990); Flavell, *Proc. Natl. Acad. Sci., USA* 91:3490-3496 (1994); Kooter and Mol, *Current Opin. Biol.* 4:166-171 (1993); and U.S. Pat. Nos. 5,034,323, 5,231,020, and 5,283,184.

Generally, where inhibition of expression is desired, some transcription of the introduced sequence occurs. The effect may occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity can exert a more effective repression of expression of the endogenous sequences. In some embodiments, sequences with substantially greater identity are used, e.g., at least about 80, at least about 95%, or 100% identity are used. As with antisense regulation, further discussed below, the effect can be designed and tested to apply to any other proteins within a similar family of genes exhibiting homology or substantial homology.

For sense suppression, the introduced sequence in the expression cassette, needing less than absolute identity, also need not be full length, relative to either the primary transcription product or fully processed mRNA. Furthermore, the introduced sequence need not have the same intron or exon pattern, and identity of non-coding segments will be equally effective. In some embodiments, a sequence of the size ranges noted above for antisense regulation is used, i.e., 30-40, or at least about 20, 50, 100, 200, 500 or more nucleotides.

Endogenous gene expression may also be suppressed by means of RNA interference (RNAi) (and indeed co-suppression can be considered a type of RNAi), which uses a double-stranded RNA having a sequence identical or similar to the sequence of the target gene. RNAi is the phenomenon in which when a double-stranded RNA having a sequence identical or similar to that of the target gene is introduced into a cell, the expressions of both the inserted exogenous gene and target endogenous gene are suppressed. The double-stranded RNA may be formed from two separate complementary RNAs or may be a single RNA with internally complementary sequences that form a double-stranded RNA. Although complete details of the mechanism of RNAi are still unknown, it is considered that the introduced double-stranded RNA is initially cleaved into small fragments, which then serve as indexes of the target gene in some manner, thereby degrading the target gene. RNAi is known to be also effective in plants (see, e.g., Chuang, C. F. & Meyerowitz, E. M., *Proc. Natl. Acad. Sci. USA* 97: 4985 (2000); Waterhouse et al., *Proc. Natl. Acad. Sci. USA* 95:13959-13964 (1998); Tabara et al. *Science* 282:430-431 (1998); Matthew, *Comp Funct Genom* 5: 240-244 (2004); Lu, et al., *Nucleic Acids Res.* 32(21):e171 (2004)).

Thus, in some embodiments, inhibition of an Snl6 gene is accomplished using RNAi techniques. For example, to achieve suppression of the expression of a DNA encoding a protein using RNAi, a double-stranded RNA having the sequence of a DNA encoding the protein, or a substantially similar sequence thereof (including those engineered not to translate the protein) or fragment thereof, is introduced into a plant of interest. As used herein, RNAi and dsRNA both refer to gene-specific silencing that is induced by the introduction of a double-stranded RNA molecule, see e.g., U.S. Pat. Nos. 6,506,559 and 6,573,099, and includes reference to a molecule that has a region that is double-stranded, e.g., a short hairpin RNA molecule. The resulting plants may then be screened for a phenotype associated with the target protein, for example, screening for an increase in the extractability of sugar from the plants as compared to wild-type plants, and/or by monitoring steady-state RNA levels for transcripts encoding the protein. Although the genes used for RNAi need not be completely identical to the target gene, they may be at least 70%, 80%, 90%, 95% or more identical to the target gene sequence. See, e.g., U.S. Patent Publication No. 2004/0029283. The constructs encoding an RNA molecule with a stem-loop structure that is unrelated to the target gene and that is positioned distally to a sequence specific for the gene of interest may also be used to inhibit target gene expression. See, e.g., U.S. Patent Publication No. 2003/0221211.

The RNAi polynucleotides may encompass the full-length target RNA or may correspond to a fragment of the target RNA. In some cases, the fragment will have fewer than 100, 200, 300, 400, 500 600, 700, 800, 900 or 1,000 nucleotides corresponding to the target sequence. In addition, in some embodiments, these fragments are at least, e.g., 50, 100, 150, 200, or more nucleotides in length. In some cases, fragments for use in RNAi will be at least substantially similar to regions of a target protein that do not occur in other proteins in the organism or may be selected to have as little similarity to other organism transcripts as possible, e.g., selected by comparison to sequences in analyzing publicly-available sequence databases.

Expression vectors that continually express siRNA in transiently- and stably-transfected have been engineered to express small hairpin RNAs, which get processed in vivo into siRNAs molecules capable of carrying out gene-specific silencing (Brummelkamp et al., *Science* 296:550-553 (2002), and Paddison, et al., *Genes & Dev.* 16:948-958 (2002)). Post-transcriptional gene silencing by double-stranded RNA is discussed in further detail by Hammond et al. *Nature Rev Gen* 2: 110-119 (2001), Fire et al. *Nature* 391: 806-811 (1998) and Timmons and Fire *Nature* 395: 854 (1998).

Yet another way to suppress expression of an endogenous plant gene is by recombinant expression of a microRNA that suppresses a target (e.g., an Snl6 gene). Artificial microRNAs are single-stranded RNAs (e.g., between 18-25-mers, generally 21-mers), that are not normally found in plants and that are processed from endogenous miRNA precursors. Their sequences are designed according to the determinants of plant miRNA target selection, such that the artificial microRNA specifically silences its intended target gene(s) and are generally described in Schwab et al, *The Plant Cell* 18:1121-1133 (2006) as well as the internet-based methods of designing such microRNAs as described therein. See also, US Patent Publication No. 2008/0313773.

One of skill in the art will recognize that using technology based on specific nucleotide sequences (e.g., antisense or sense suppression, siRNA, microRNA technology, etc.), families of homologous genes can be suppressed with a single sense or antisense transcript. For instance, if a sense or antisense transcript is designed to have a sequence that is conserved among a family of genes, then multiple members of a gene family can be suppressed. Conversely, if the goal is to only suppress one member of a homologous gene family, then the sense or antisense transcript should be targeted to sequences with the most variance between family members.

Alternatively, random mutagenesis approaches may be used to disrupt or "knockout" the expression of an Snl6 gene using either chemical or insertional mutagenesis, or irradiation. One method of mutagenesis and mutant identification is known as TILLING (for targeting induced local lesions in genomes). In this method, mutations are induced in the seed of a plant of interest, for example, using EMS treatment. The resulting plants are grown and self-fertilized, and the progeny are assessed. For example, the plants may be assayed using PCR to identify whether a mutated plant has an Snl6 mutation, e.g., that reduces expression of an Snl6 gene, or by evaluating whether the plant has reduced levels of phenolics or increased sugar extractability, or decreased lignin content in a part of the plant that expressed the Snl6 gene. TILLING can identify mutations that may alter the expression of specific genes or the activity of proteins encoded by these genes (see Colbert et al (2001) Plant Physiol 126:480-484; McCallum et al (2000) Nature Biotechnology 18:455-457).

The invention also provides "knockout Snl6 plants" where mutagenesis, e.g., disruption of a Snl6 gene sequence by, e.g., homologous recombination, leads to loss of expression of the endogenous gene. Methods of generating "knockout" plants are well-known in the art, see, e.g., Strepp (1998) Proc Natl. Acad. Sci. USA 95:4368-4373; Miao (1995) Plant J 7:359-365. See discussion on transgenic plants, below.

Another method for abolishing or decreasing the expression of an Snl6 gene is by insertion mutagenesis using the T-DNA of *Agrobacterium tumefaciens*. After generating the insertion mutants, the mutants can be screened to identify those containing the insertion in an Snl6 gene. Mutants containing a single mutation event at the desired gene may be crossed to generate homozygous plants for the mutation (Koncz et al. (1992) Methods in *Arabidopsis* Research. World Scientific).

Another method to disrupt an Snl6 gene is by use of the cre-lox system (for example, as described in U.S. Pat. No. 5,658,772).

In further embodiments, Snl6 gene expression can be disrupted by targeting a promoter that controls expression of the endogenous Snl6 gene. The promoter is 5' to the transcription start site and typically includes from 250-500, or to 1000 or to 1500 base pairs upstream of the transcription start site.

Preparation of Recombinant Vectors

To use isolated sequences in the above techniques, recombinant expression vectors suitable for transformation of plant cells such as crop plant cells are prepared. For example, a polynucleotide sequence encoding a sequence that inhibits expression of an endogenous Snl6 gene (described in further detail herein) can be combined with transcriptional and other regulatory sequences which will direct the transcription of the sequence from the gene in the intended cells, e.g., rice or other crop plant cells. Typically, plant transformation vectors include one or more cloned plant coding sequences (genomic or cDNA) under the transcriptional control of 5' and 3' regulatory sequences and a dominant selectable marker. Such plant transformation vectors typically also contain a promoter (e.g., a regulatory region controlling inducible or constitutive, environmentally- or developmentally-regulated, or cell- or tissue-specific expression), a transcription initiation start site, an RNA processing signal (such as intron splice sites), a transcription termination site, and/or a polyadenylation signal.

In some embodiments, a constitutive plant promoter may be used for directing expression of the polynucleotide in all tissues of the plant. Examples of constitutive plant promoters include: the cauliflower mosaic virus (CaMV) 35S promoter, which confers constitutive, high-level expression in most plant tissues (see, e.g., Odel et al., (1985) Nature 313:810); the nopaline synthase promoter (An et al., (1988) Plant Physiol. 88:547); and the octopine synthase promoter (Fromm et al., (1989) Plant Cell 1:977). Additional constitutive regulatory elements, including those for efficient expression in monocots, also are known in the art, for example, the pEmu promoter and promoters based on the rice Actin-1 5' region (Last et al., *Theor. Appl. Genet.* 81:581 (1991); Mcelroy et al., *Mol. Gen. Genet.* 231:150 (1991); Mcelroy et al., *Plant Cell* 2:163 (1990)).

Alternatively, the plant promoter may direct expression of the polynucleotide of the invention in a specific tissue (tissue-specific promoters). Tissue specific promoters are transcriptional control elements that are only active in particular cells or tissues at specific times during plant development, such as in vegetative tissues or reproductive tissues. Examples of tissue-specific promoters include promoters that initiate transcription primarily in certain tissues, such as vegetative tissues, e.g., roots or leaves, or reproductive tissues, such as fruit, ovules, seeds, pollen, pistols, flowers, or any embryonic tissue. Other examples are promoters that direct expression specifically to cells and tissues with secondary cell wall deposition, such as xylem and fibers.

Alternatively, the plant promoter may be under more precise environmental control (inducible promoters). Examples of environmental conditions that may affect transcription by inducible promoters include anaerobic conditions, elevated temperature, drought, or the presence of light. Examples of environmental promoters include drought-inducible promoter of maize (Busk (1997) supra); the cold, drought, and high salt inducible promoter from potato (Kirch (1997) *Plant Mol. Biol.* 33:897 909). Plant promoters that are inducible upon exposure to plant hormones, such as auxins, may also be employed. For example, the invention can use the auxin response elements E1 promoter fragment (AuxREs) in the soybean (*Glycine max* L.) (Liu (1997) *Plant Physiol.* 115:397 407); the auxin-responsive *Arabidopsis* GST6 promoter (also responsive to salicylic acid and hydrogen peroxide) (Chen (1996) *Plant J.* 10: 955 966); the auxin-inducible parC promoter from tobacco (Sakai (1996) 37:906 913); a plant biotin response element (Streit (1997) *Mol. Plant Microbe Interact.* 10:933 937); and, the promoter responsive to the stress hormone abscisic acid (Sheen (1996) *Science* 274:1900 1902).

Plant promoters which are inducible upon exposure to chemical reagents that can be applied to the plant, such as herbicides or antibiotics, may also be used in vectors as described herein. For example, the maize In2 2 promoter, activated by benzenesulfonamide herbicide safeners, can be used; application of different herbicide safeners induces distinct gene expression patterns, including expression in the root, hydathodes, and the shoot apical meristem. Other promoters, e.g., a tetracycline inducible promoter; a salicylic acid responsive element promoter, promoters comprising copper-inducible regulatory elements; promoters comprising ecdysone inducible regulatory elements; heat shock inducible promoters, a nitrate-inducible promoter, or a light-inducible promoter may also be used.

Plant expression vectors may also include RNA processing signals that may be positioned within, upstream or downstream of the coding sequence. In addition, the expression vectors may include additional regulatory sequences from the 3'-untranslated region of plant genes, e.g., a 3' terminator region to increase mRNA stability of the mRNA, such as the PI-II terminator region of potato or the octopine or nopaline synthase 3' terminator regions.

Plant expression vectors routinely also include dominant selectable marker genes to allow for the ready selection of transformants. Such genes include those encoding antibiotic resistance genes (e.g., resistance to hygromycin, kanamycin, bleomycin, G418, streptomycin or spectinomycin), herbicide resistance genes (e.g., phosphinothricin acetyltransferase), and genes encoding positive selection enzymes (e.g. mannose isomerase).

Once an expression cassette comprising a polynucleotide encoding an inhibitor of the expression of an Snl6 gene has been constructed, standard techniques may be used to introduce the polynucleotide into a plant in order to modify Snl6 activity and accordingly, the synthesis of phenolics in the plant or plant part in which the Snl6 target nucleic acid is expressed. See protocols described in Ammirato et al. (1984) Handbook of Plant Cell Culture—Crop Species. Macmillan Publ. Co. Shimamoto et al. (1989) Nature 338:274-276; Fromm et al. (1990) Bio/Technology 8:833-839; and Vasil et al. (1990) Bio/Technology 8:429-434.

Transformation and regeneration of plants is known in the art, and the selection of the most appropriate transformation technique will be determined by the practitioner. Suitable methods may include, but are not limited to: electroporation of plant protoplasts; liposome-mediated transformation; polyethylene glycol (PEG) mediated transformation; transformation using viruses; micro-injection of plant cells; micro-projectile bombardment of plant cells; vacuum infiltration; and *Agrobacterium tumeficiens* mediated transformation. Transformation means introducing a nucleotide sequence in a plant in a manner to cause stable or transient expression of the sequence. Examples of these methods in various plants include: U.S. Pat. Nos. 5,571,706; 5,677,175; 5,510,471; 5,750,386; 5,597,945; 5,589,615; 5,750,871; 5,268,526; 5,780,708; 5,538,880; 5,773,269; 5,736,369 and 5,610,042.

Following transformation, plants are preferably selected using a dominant selectable marker incorporated into the transformation vector. Typically, such a marker will confer antibiotic or herbicide resistance on the transformed plants or the ability to grow on a specific substrate, and selection of transformants can be accomplished by exposing the plants to appropriate concentrations of the antibiotic, herbicide, or substrate.

Snl6 nucleic acids can be obtained using many methods known in the art. Such methods can involve amplification reactions such as PCR and other hybridization-based reactions or can be directly synthesized.

Screening for Plants Having Suppressed Snl6 Expression

After transformed plants are selected, parts of the plants may be evaluated to determine the level of Snl6 gene expression in a part of the plant that expresses the Snl6 gene, e.g., by evaluating the level of RNA or protein, by determining the amounts of soluble sugars that can be extracted from the plants, or by evaluating the synthesis of phenolics and/or lignin present in the plants. These analyses can be performed using any number of methods known in the art.

In some embodiments, the amount of soluble sugar that can be extracted from a plant can be measured by a saccharification reaction, e.g., enzymatic saccharification. Methods of enzymatic saccharification are known in the art. Briefly, plants or plant biomass material (e.g., leaves and stems) are pre-treated with hot water or dilute acid, followed by enzymatic saccharification using a mixture of cellulose and beta-glucosidase in buffer and incubation of the plants or plant biomass material with the enzymatic mixture. Following incubation, the yield of the saccharification reaction can be readily determined by measuring the amount of reducing sugar released, using a standard method for sugar detection, e.g. the dinitrosalicylic acid method well known to those skilled in the art. Plants engineered in accordance with the invention provide a higher sugar yield.

Alternatively, the level of Snl6 gene expression can be assessed by measuring the phenolic content in the plant. Methods of measuring phenolic content are known in the art, see, e.g., Fitzgerald et al., Mol Plant Microbe Interact. 17:140-151 (2004), incorporated herein by reference for all purposes.

Plants of the invention that exhibit reduced Snl6 gene expression have at least a 5% increase in sugar obtained from a reaction, e.g., as assessed by a saccharification reaction, typically at least 10% increase in sugar extractability, or more often at least 15%, 20%, 30%, 40%, or 50% or more increase in sugar compared to a plant that has not been engineered to decrease expression of the Snl6 gene. As understood in the art, Snl6-mediated increase in sugar extractability may occur in one or more parts of the plants, e.g., sugar extractability may be increased in a leaf and/or a stem.

Plants of the invention that exhibit reduced Snl6 gene expression can also have a lignin content that is reduced by at least 10%, often by at least 15%, at least 20%, at least 30%, at least 40%, or at least 50% compared to a plant that has not been engineered to decrease expression of the Snl6 gene. As understood in the art, Snl6-mediated decrease in lignin content may occur in one or more parts of the plants, e.g., lignin content may be decreased in the stem.

Plants, plant biomass material, or bulk harvested material from plants having reduced Snl6 expression can be used in a variety of reactions, including fermentation reactions. Such reactions are well known in the art. For example, fermentation reactions such as yeast or bacterial fermentation reactions may employ plants of the present invention to obtain ethanol, butanol, lipids, and the like. For example, the plants may be used in industrial bioprocessing reactions that include fermentative bacteria, yeast, or filamentous fungi.

EXAMPLES

Example 1: Identification and Characterization of Snl6 Mutant

Snl6 was identified through a mutagenesis screen to identify components of the rice innate immune response. Plant innate immunity is governed by a complex signaling network [1]. Hallmark events during the immune response include localized cell death at the site of pathogen recognition (known as the hypersensitive response (HR)), release of reactive oxygen species (ROS), pathogen related (PR) gene induction, callose deposition and cell wall lignification [2-4]. The HR, ROS and PR gene production are thought to be physically harmful towards the invading pathogen while callose and lignin deposition create a physical barrier to limit pathogen entry and spread [4-8]. NPR1 (Non-expresser of PR genes-1) is a central regulator of the disease response in *Arabidopsis* and has been studied extensively [9-13]. Plants deficient in NPR1 expression lack PR gene accumulation after pathogen treatment, display increased susceptibility to pathogens and fail to initiate systemic acquired resistance (SAR) [11]. Over-expression of the rice NPR1 ortholog, NH1 (NPR1 homologue 1) (NH1ox) in rice results in enhanced resistance to the bacterial pathogen *Xanthomonas oryzae* pv. *oryzae* (Xoo), constitutive expression of PR genes and a BTH (benzothiadiazole)-mediated cell death phenotype [14]. Enhanced cell death (also called lesion mimic phenotypes) has been correlated with resistance [15, 16].

Identification of the Snl6 Mutant that Suppresses NH1-Mediated Lesion Formation.

We have previously reported that overexpression of the rice NPR1 homologue, NH1, in a LiaoGeng (LG) background, confers resistance to the bacterial pathogen *Xanthomonas oryzae* pv. *oryzae* (Xoo) and leads to a spontaneous cell death phenotype [14]. The cell death phenotype is enhanced by application of the salicyclic acid functional analog BTH [27]. We designed a screen to identify mutants incapable of developing this cell death phenotype (FIG. 1A). NH1ox seeds were treated with fast neutron (FN) mutagenesis. $M_1$ progeny from 4,000 $M_0$ were harvested in the rice field. Approximately 60,000 $M_1$ individuals were grown in the rice field and sprayed with 10 mM BTH at 5 weeks and 7 weeks and scored for cell death at 10 weeks. BTH treatment of NH1ox plants in the field resulted in cell death, visualized by discrete lesions on the leaves. While most plants showed the typical NH cell death phenotype, approximately 20 plants showed little to no cell death and were therefore named suppressor of BTH-induced, NH1-mediated lesion mimic (snl) mutants. The suppressed cell death phenotype of snl6-FN (fast neutron allele) was confirmed in the greenhouse (FIG. 1B).

Figure 2:
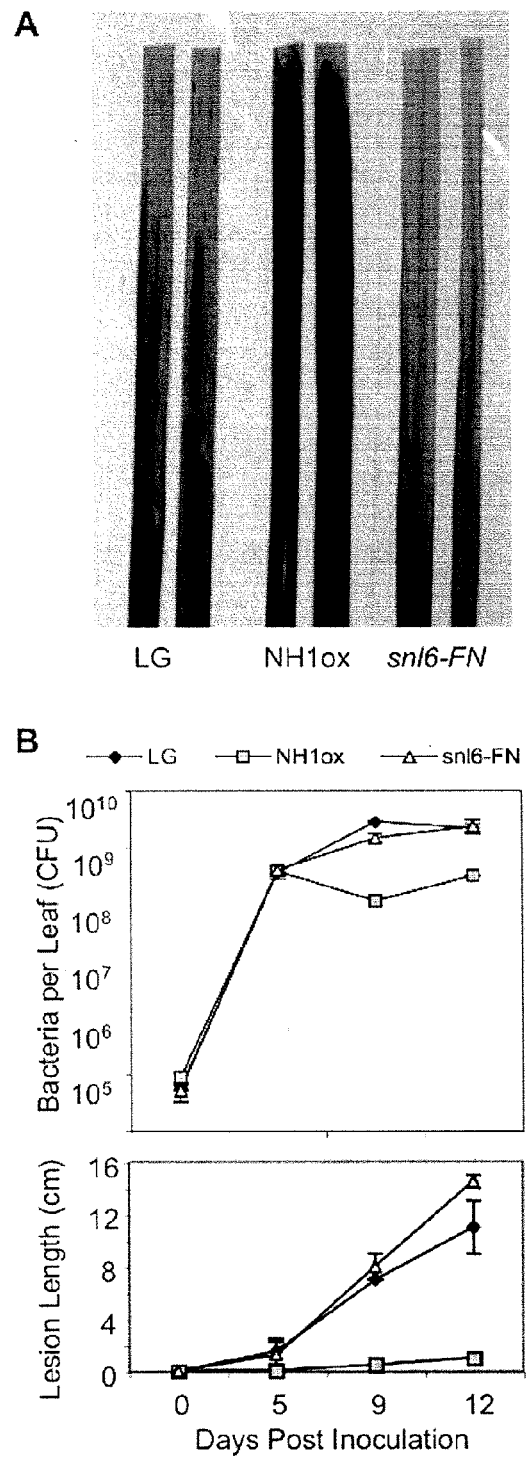
FIG. 2. Snl6 is required for NH1ox-mediated resistance to Xoo. 8-week old plants were challenged with Xoo. (A) Lesion length development after 12 days. (B) Total bacterial populations per leaf (top) and lesion lengths (bottom) were measured at 0, 5, 9 and 12 days post inoculation. Mean, ±range (n=2), are displayed. The growth curve experiment was repeated twice with similar results. LG, NH1ox and snl6-FN (line: 11-3-2) were compared.
Figure 8:
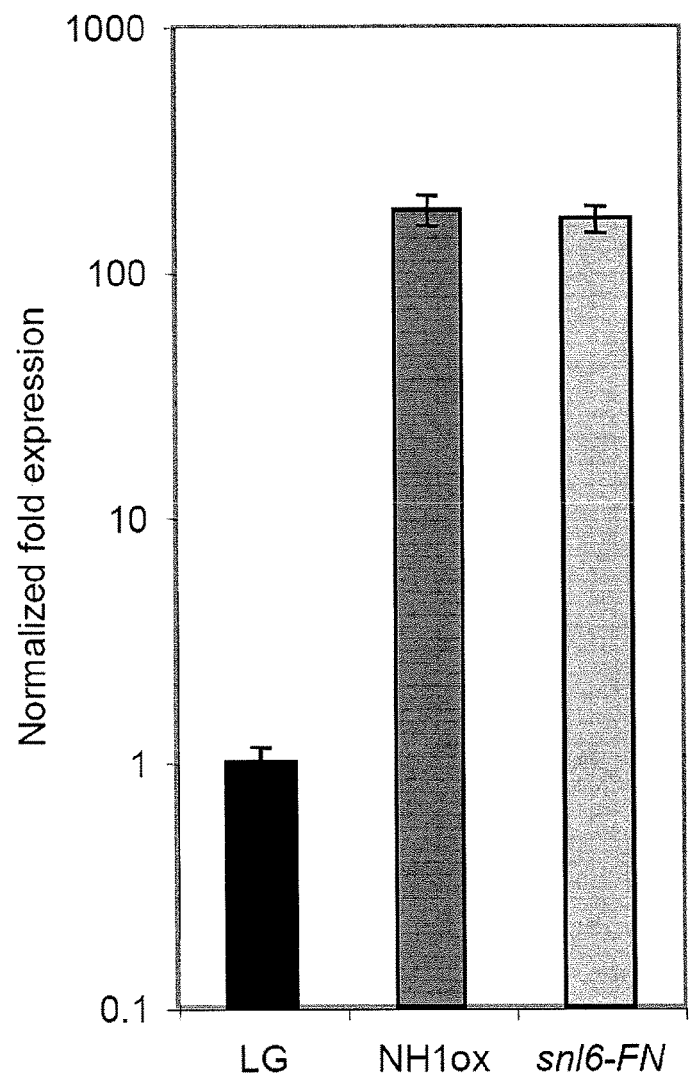
FIG. 8. snl6-FN overexpresses NH1. Quantitative RT-PCR was used to determine the relative amounts of NH1 expression in LG, NH1ox, and snl6-FN (line: 11-3-2-1) plants. Mean±s.e.m, n=3.

As lesion mimic mutants often have an accompanying resistance phenotype [15, 16], we hypothesized that snl6-FN plants may show enhanced susceptibility to Xoo. Indeed, snl6-FN lines show longer water-soaked lesions after infection with Xoo and support greater populations of Xoo cells than NH1ox plants (FIG. 2A, B), indicating that Snl6 is required for NH1-mediated resistance. To ensure that the snl6-FN phenotype did not represent a mutation in the NH1 overexpression transgene, we confirmed the overexpression of NH1 in the snl6-FN line (FIG. 8).

Comparative Genome Hybridization Combined with Fine Mapping Locate Snl6 on Rice Chromosome 1.

Conventional map-based cloning, while effective, is slow and laborious [25, 28]. With the availability of fully sequenced genomes, an alternative method for gene cloning has emerged called comparative genome hybridization (CGH) [29]. CGH uses tiling arrays to physically compare two genomes. In CGH, genomic DNA from each plant is fragmented and differentially labeled. The labeled DNA is then hybridized to a tiling array, composed of probes where each probe corresponds to a known location on the reference genome. Probes that show strong hybridization with the parent but not the mutant indicate deleted regions on the mutant genome. Because the snl6-FN mutant was created with fast neutron mutagenesis, which generally induces deletions on chromosomes [30], we employed CGH to expedite the cloning of Snl6. In collaboration with Nimblegen, we designed a full genome tiling array for rice (*japonica* cultivar) with an average probe spacing of one 50-mer probe every 146 bp. NH1ox and snl6-FN genomic DNA were prepared, fragmented and labeled with Cy3 or Cy5, respectively. Relative hybridization intensities for each probe are reported as: $\log_2$(snl6-FN/NH1ox). A negative $\log_2$ ratio represents a deletion in the genome of the snl6-FN mutant. CGH revealed 5 deletions (FIG. 3A), encompassing 35 annotated genes (FIG. 14), in the genome of snl6-FN and each was confirmed through PCR.

Figure 3:
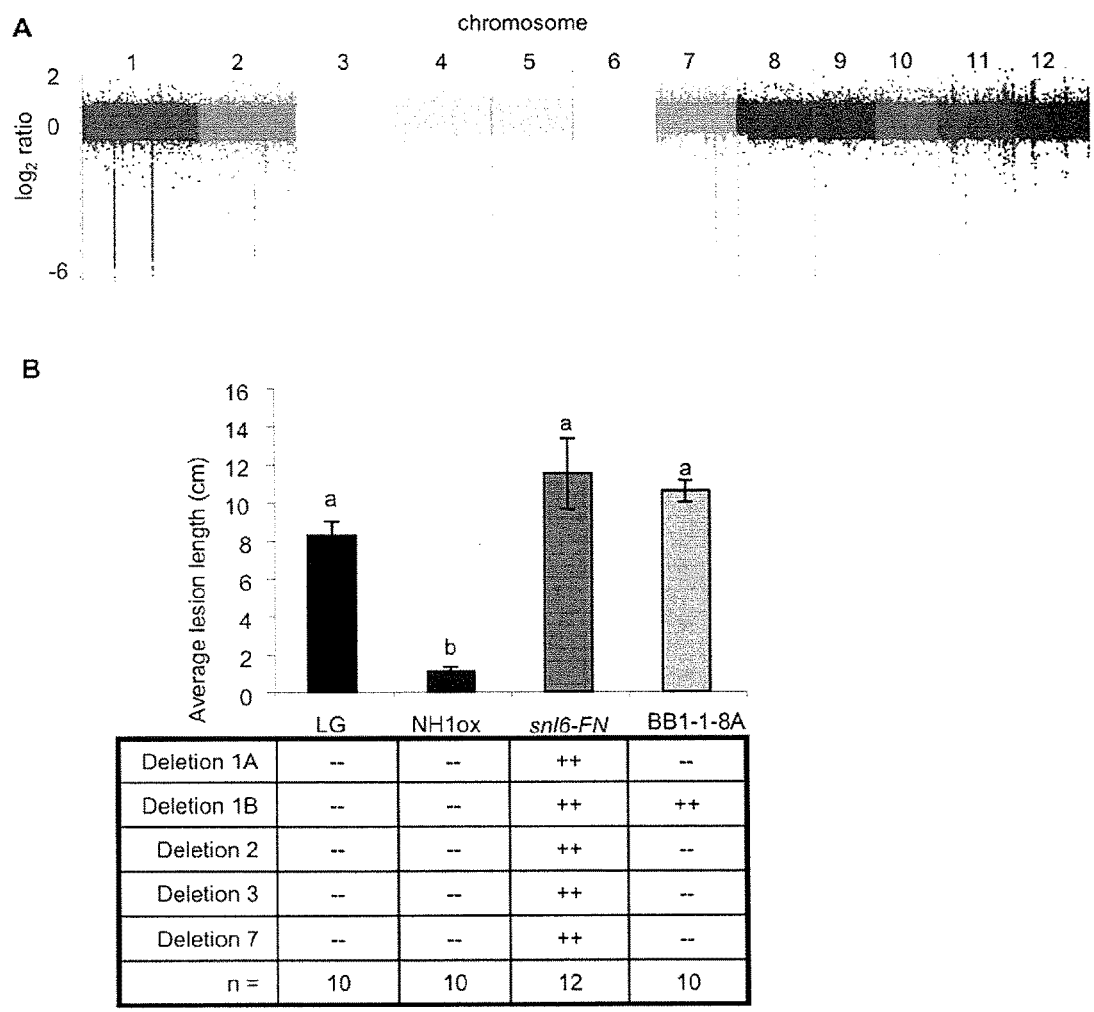
FIG. 3. Snl6 segregates with deletion 1B. (A) Comparative Genome Hybridization (CGH) between NH1ox and snl6-FN (line: 11-3-2). Each spot represents an average of all probes in a 1.5 kb region. Identified deletions were named based on chromosome number as follows Deletion 1A, 1B, 2, 3, 7. (B) Plants were scored for resistance after challenge with Xoo. mean±s.e.m, Different letters represent significant difference (p<0.05). LG, NH1ox, snl6-FN (line 11-3-2), BB1-1-8A (F2 mapping population individual) progeny.

Next, we created an F2 mapping population (line: BB1-1) and individuals were genotyped for the NH1ox transgene, each deletion and then scored for resistance to Xoo. Only the second deletion on chromosome 1 (Deletion 1B) co-segregated completely with susceptibility. One individual showed a recombination event between the two deletions on chromosome 1. We analyzed the next generation of this line (BB1-1-8A) and confirmed the susceptibility (FIG. 3B). Deletion 1B contains 3 annotated, non-transposon genes: LOC_Os01g45160, LOC_OS01g45190 and LOC_Os01g45200 (FIG. 14). The former does not have any associated expression data (based on EST libraries and publicly available microarray data) and thus we de-prioritized this gene as an unlikely candidate for Snl6. LOC_Os01g45200 is annotated as a cinnamoyl CoA-reductase (CCR)-like gene (TIGR v6.1). Because CCRs catalyze the first committed step in the lignin biosynthetic pathway and have previously been linked to the defense response [31, 32], LOC_Os01g45200 became our top candidate for Snl6.

Snl6 Encodes a Member of the Cinnamoyl CoA-Reductase (CCR)-Like Gene Family.

Figure 4:
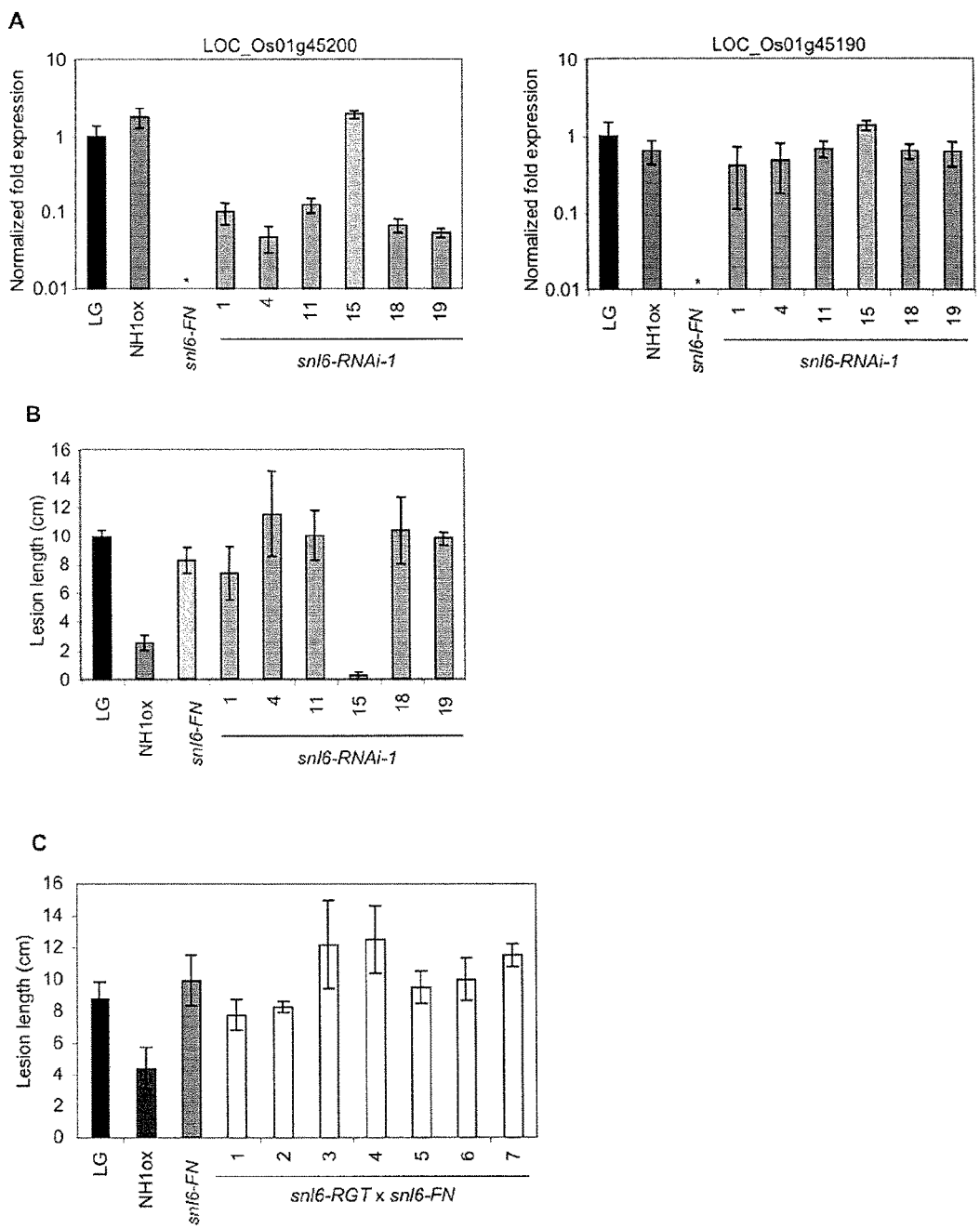
FIG. 4. RNAi and allelic complementation for Snl6. (A) Expression of LOC_Os01g45190 and LOC_Os01g45200 in snl6-RNAi-1 progeny, ±s.d., n=3. (B) Lesion lengths of snl6-RNAi-1 T1 progeny, 14 days after inoculation with Xoo.±s.d., n=3; *=expression level below background. (C) Allelic complementation test. Lesion lengths 11 days after challenge with Xoo.±s.d., n=3. LG, NH1ox, snl6-FN (line 11-3-2), snl6-RNAi-1 progeny ($T_1$), snl6-RGT (RGT6140B_5.1) x snl6-FN (line: 11-3-2) F1 individuals.
Figure 9:
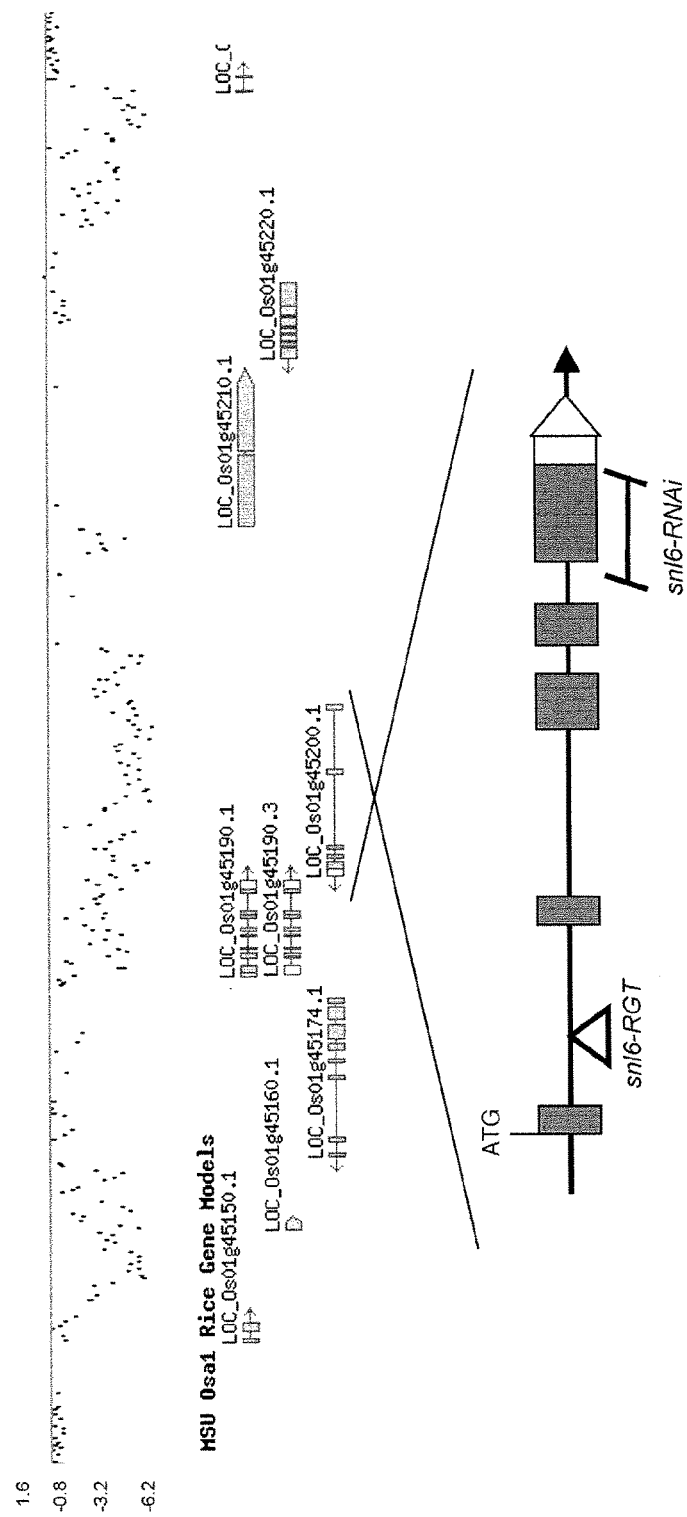
FIG. 9. Annotated genes in Deletion 1B and schematic of snl6 RNAi and insertion line. (Top) CGH results for Deletion 1B showing predicted gene models. Gene annotation is based on TIGR v 5. (Bottom) Schematic of snl6-RNAi and snl6-RGT. An inverted repeat RNAi construct was created to silence Os01g45200. PCR was used to amplify the 3' end of Os01g45200 and the resulting fragment was cloned in inverse orientation, separated by an approximately 1 kb spacer. To identify the location of the insertion in snl6-RGT (line: RGT6140B_5.1), insertion specific primers (Ds5'-2a) were combined with primers specific to Os01 g45200. The resulting PCR product was sequenced and revealed that the insertion is in the first intron of Os01g45200.
Figure 10:
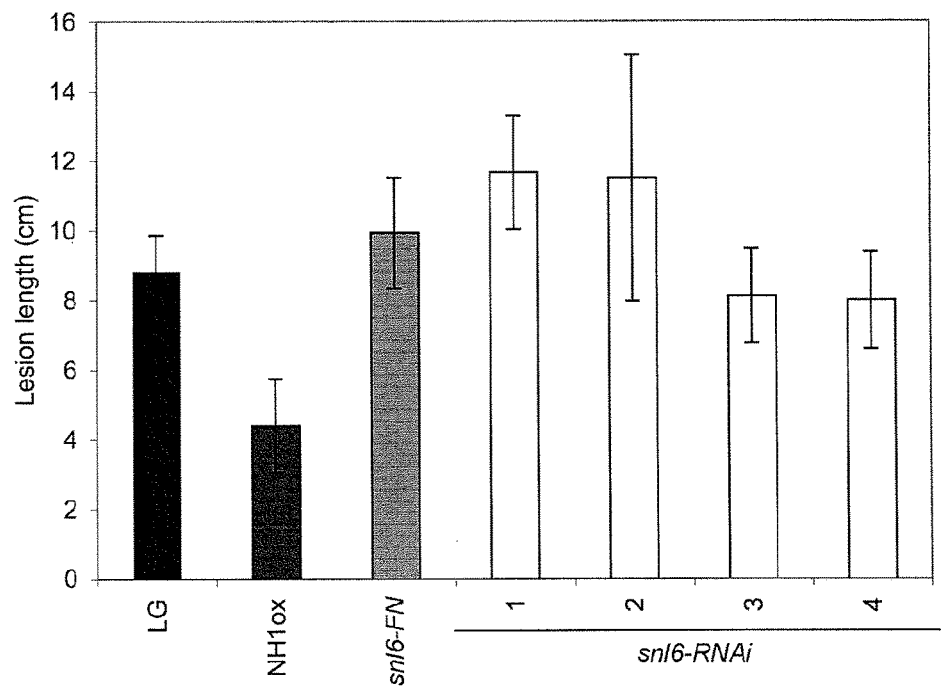
FIG. 10. Four snl6-RNAi $T_0$ lines are susceptible to Xoo. 8-week-old independently transformed lines were challenged with Xoo and lesion length development measured after 12 days. Mean±s.e.m, n=3 are displayed.

To determine if LOC_Os01g45200 is Snl6, we generated transgenic plants expressing an inverted repeat RNAi construct (snl6-RNAi) to silence LOC_Os01g45200 in an NH1ox background (FIG. 9). snl6-RNAi targets 425 bp of the 3' end of LOC_Os01g45200. This region is 74% identical to the closest homolog, LOC_Os05g50250, however because LOC_Os05g50250 is intact in the snl6-FN and snl6-RGT alleles (as described below), we concluded that LOC_Os05g50250 does not contribute to the snl6 mutant phenotype. Four independent RNAi lines (primary transgenics, $T_0$) challenged with Xoo displayed enhanced susceptibility as compared to the NH1ox control (FIG. 10). Among six $T_1$ progeny of snl6-RNAi-1, the enhanced susceptibility phenotype segregated perfectly with the presence of the transgene and with reduced expression of LOC_Os01g45200 (FIG. 4A, B). LOC_Os01g45190 showed wild-type expression levels in all snl6-RNAi-1 progeny indicating that this gene does not contribute to the snl6 susceptibility phenotype. While snl6-RNAi-1 shows higher expression of Snl6 than the deletion allele, snl6-FN, the resulting lesion lengths for these different lines are comparable suggesting that Snl6 may not function in a dosage dependent manner. Next, we identified an insertion line from the Rice Transposon Flanking Sequence Tag (FST) Database [33]. We designated this line snl6-RGT (FIG. 9) and performed an allelic complementation test by crossing snl6-RGT with snl6-FN (recessive) and analyzing the progeny. Successful crosses were confirmed through PCR. All seven F1 individuals challenged with Xoo showed levels of enhanced susceptibility similar to that of snl6-FN (FIG. 4C). These lines carry one copy of the NH1ox transgene, which we have previously shown is sufficient to confer high levels of resistance to Xoo [14]. Thus we conclude that snl6-RGT and snl6-FN are allelic. Taken together these data confirm that LOC_Os01g45200 is snl6, a cinnamoyl-CoA reductase (CCR)-like gene.

Snl6 encodes a predicted protein of 364 amino acids (39.5 kDa). CCRs exist as multi-gene families with at least 7 and 14 annotated members in *Arabidopsis* and rice, respectively. Previously described CCR genes show limited identity with snl6 [31, 32, 34, 35] (FIG. 11). The closest predicted rice paralog is LOC_Os05g50250, sharing 73% identity at the amino acid level. Sorghum, *Brachypodium* and maize all have predicted orthologs (EES03334.1, 2g44800.1 and ACR34585.1 with 86%, 81% and 82%, amino acid identity, respectively). The closest predicted ortholog in *Arabidopsis thaliana* is AT5G14700 with 44% amino acid identity. None of these closest predicted orthologs have been functionally characterized. In *Arabidopsis*, the more distantly related genes AtCCR1 (25% identity) and AtCCR2 (27% identity) have been attributed a primary role in development or pathogen attack, respectively. They appear to be able to partially compensate for each other [32].

Snl6 is not Required for XA21-Mediated Resistance.

Figure 5:
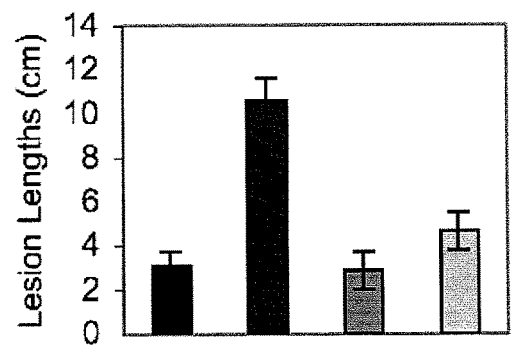
FIG. 5. Snl6 contributes to resistance in the absence of NH1ox. (A) Individuals from line BB1-1 (snl6-FN (line: 11-3-2) x Ubi-Xa21-kitaake (line 7A-8)) were genotyped for the presence of NH1ox, Xa21 and Snl6. 8-week old plants were moved to the growth chamber and challenged with Xoo. Lesion lengths were measured after 12 days. Mean s.e.m. and number of individuals (n) are reported. (B) Average lesion lengths 11 days after Xoo inoculation. Nip (wildtype cultivar nipponbare); snl6-RGT (T-DNA insertion in Snl6). s.e.m., n=12 (nip) or 18 (snl6-RGT). Letters (a, b) indicate significant difference (p<0.05).
Figure 5:
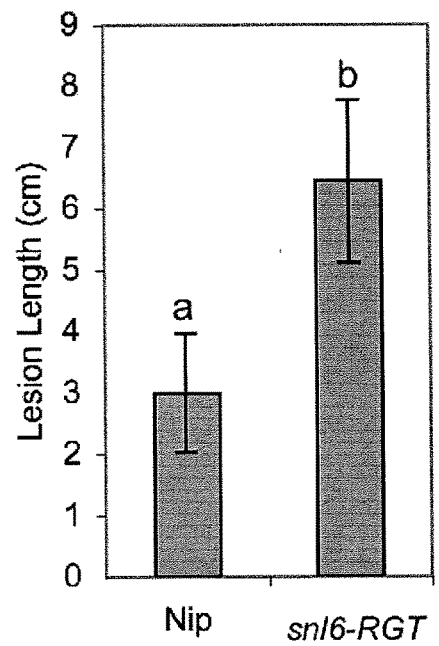

Both NH1ox and XA21-mediated resistance are regulated by NRR (negative regulator of resistance) suggesting a possible overlap of these pathways [36]. To determine if Snl6 is required for resistance mediated by XA21, we examined individual F2 progeny derived from a cross between snl6-FN line and a transgenic line expressing Xa21 under control of the ubiquitin promoter [37]. These lines were segregating for NH1ox, Xa21 and Snl6. Plants containing Xa21 were resistant to Xoo independent of the presence of Snl6 (FIG. 5A). Thus we conclude that Snl6 is required for NH1-mediated resistance, but not XA21-mediated resistance in these lines. Our results are consistent with studies from *Arabidopsis* showing that the PRR, FLS2, does not require NPR1 to initiate an immune response [38].

Snl6 Contributes to Resistance in the Absence of NH1ox.

We have shown that Snl6 contributes to NH1ox-mediated resistance. To further investigate the role of Snl6 in the absence of NH1ox we compared inoculation data for snl6-RGT (lacking the NH1ox transgene) and in the genetic background of cultivar, Nipponbare used as a recipient in the transformation studies. While both lines are susceptible to inoculation with Xoo, snl6-RGT plants developed longer lesions suggesting that Snl6 contributes to resistance in Nipponbare (FIG. 5B).

Snl6 is Required for NH1-Mediated PR10 Gene Expression.

Figure 6:
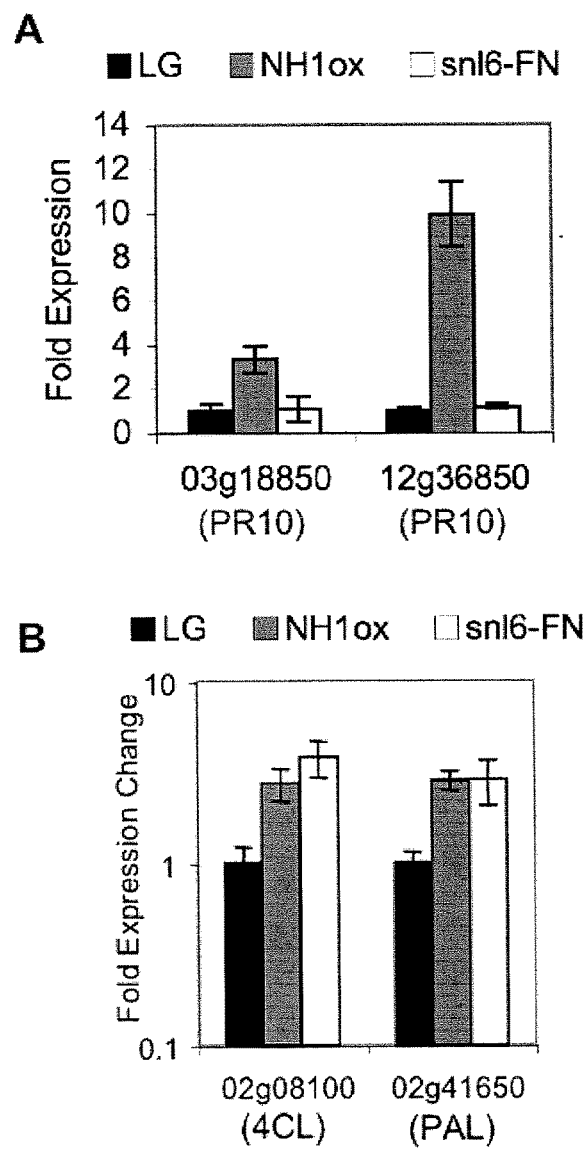
FIG. 6. Characterization of the role of Snl6 in the defense response. Relative gene expression levels in LG, NH1ox and snl6-FN (line: 11-3-2-1) lines using realtime quantitative RT-PCR, (A) two PR10 genes (B) 4CL and PAL; mean±s.e.m, n=3.

The NH1ox resistance phenotype is correlated with constitutively high expression levels of several PR genes [14]. To further elucidate the role of Snl6 in innate immunity, we examined the relative expression levels of two PR10/PBZ family members (LOC_Os03g18850 and LOC_Os12g36850), in LG, NH1ox and snl6-FN lines. Both PR10 family members show significantly higher expression levels in NH1ox lines as compared to LG. snl6-FN lines, while still over-expressing NH1 (FIG. 8), do not show enhanced PR10/PBZ gene expression (FIG. 6A). A similar result was observed for the snl6-RNAi-1 line.

PAL and 4-Coumarate-CoA Ligase 1 (4CL) are Co-Expressed with Snl6.

In addition to induced PR gene expression, overexpression of NH1 results in constitutive activation of phenylalanine ammonia-lyase (PAL). PAL catalyzes the first step of the highly branched phenylpropanoid pathway and has been studied for its role in lignin biosynthesis as well as defense related molecules such as salicylic acid. By analyzing publicly available microarray data we found that PAL as well as a member of the lignin specific branch of the phenylpropanoid biosynthetic pathway, 4-coumarate-CoA ligase 1 (4CL), were highly co-expressed (cc>0.6) with Snl6. We hypothesized that snl6 mutant lines might contain alterations in the phenylpropanoid pathway. Both PAL and 4CL showed more than 2 fold higher expression in NH1ox and snl6-FN as compared to LG (FIG. 6B). These results indicate that lignin biosynthesis is induced by over expression of NH1 and further suggest that Snl6 may function downstream of PAL and 4CL, which would be consistent with the published placement of CCR in the phenylpropanoid pathway.

Snl6 Mutants have Reduced Lignin and Enhanced Sugar Extractability.

Figure 7:
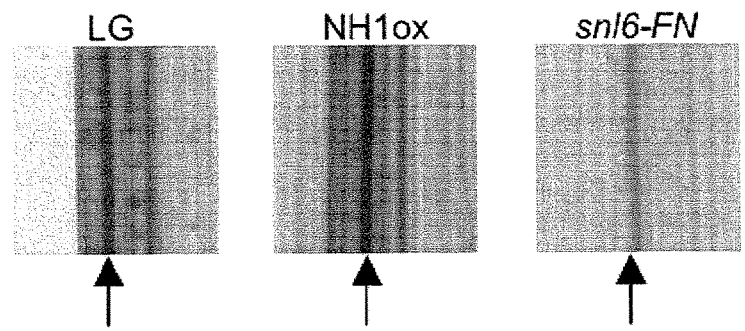
FIG. 7. Characterization of the role of Snl6 in the phenylpropanoid pathway. Tissue from 8-week old plants was cleared with lactic acid/phenol and stained with phloroglucinol/HCl. Images were taken at 2× magnification. Arrows point to the midrib of each sample. Experiment was repeated 5 times with similar results. Note: LG sample ripped during sample preparation.
Figure 12:
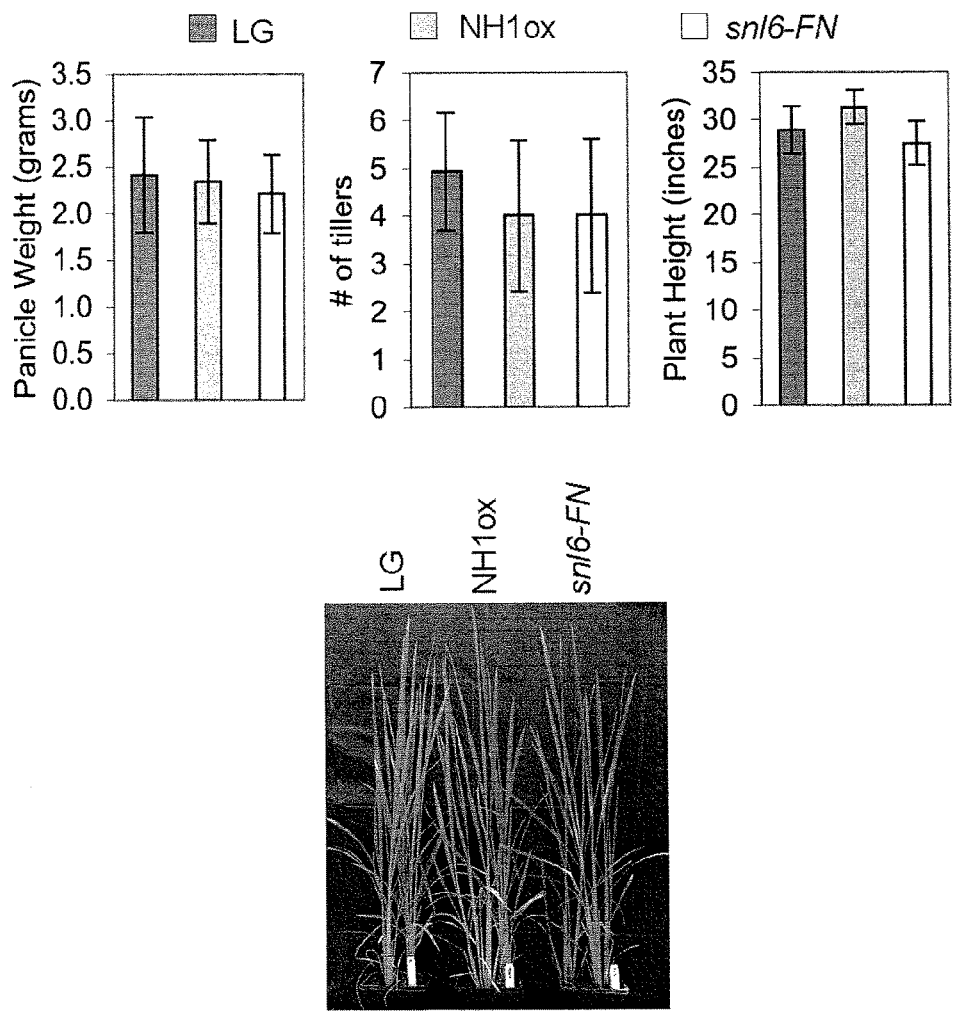
FIG. 12. snl6 mutants display no obvious developmental defects. Plant height and tiller number were evaluated at 8 weeks and a picture was taken of each genotype. Seed set was evaluated (total panicle weight) after senescence. LG, NH1ox, and snl6-FN (line 11-3-2-1) are compared.

To further elucidate the function of Snl6, we used the Wiesner Test (Phloroglucinol/HCl). Phloroglucinol/HCl reacts with aromatic aldehydes to produce a pink/red color and is commonly used to detect lignin [34, 39, 40]. NH1ox and LG showed clear staining, most strongly at the midvein (arrow). While some staining is observed in snl6-FN leaves, total staining is reduced especially at the midvein (FIG. 7). Among five independent experiments, the amount of staining observed in LG leaves varied, but was consistently greater than that seen for snl6 mutant line suggesting that additional environmental factors contribute to wild-type lignin accumulation. Notably, most previously characterized lignin mutants express a severe developmental phenotype [34, 40-42]. In contrast, no significant difference was found between snl6-FN and wild-type plants for plant height, seed set, tiller number or general appearance (FIG. 12).

Figure 13:
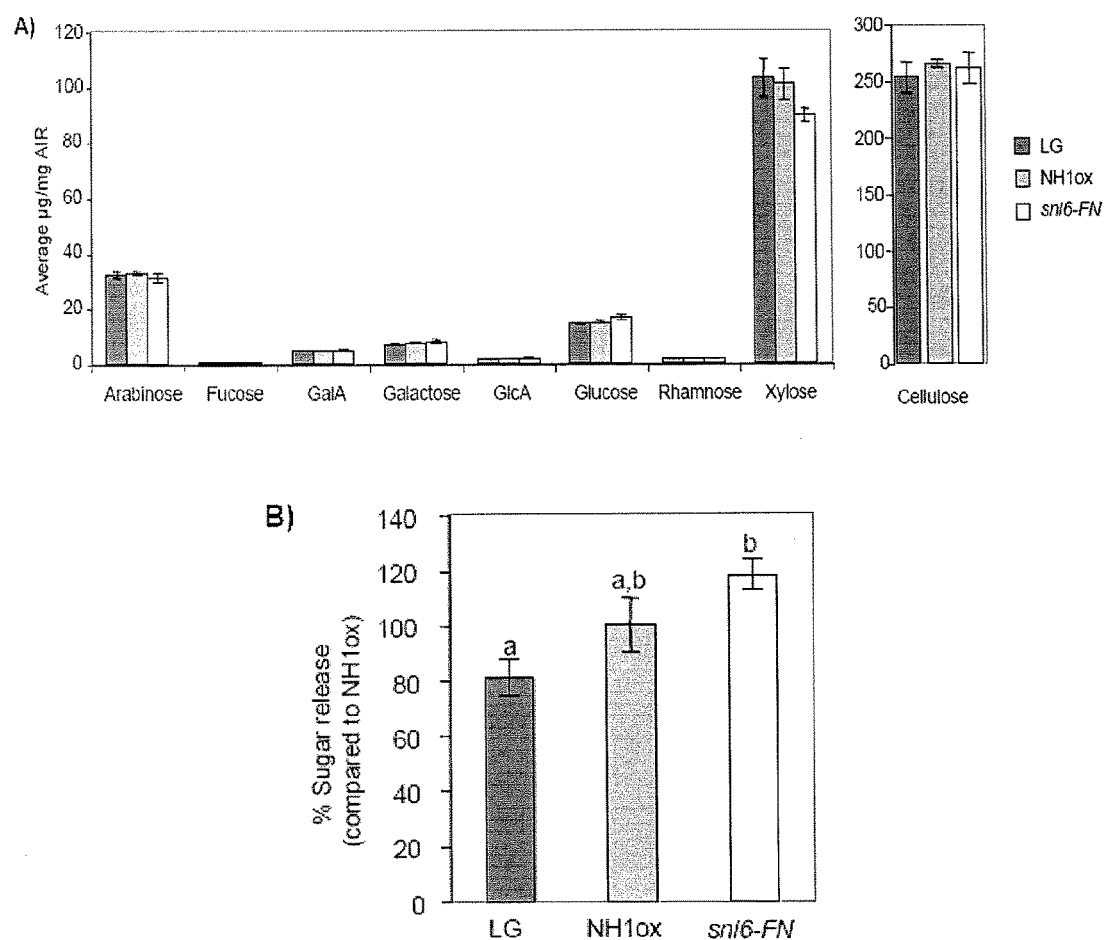
FIG. 13. Sugar analysis reveals higher sugar release from snl6 mutant lines. Cell wall extraction (AIR) was performed on LG, NH1ox, and snl6-FN (lines 11-3-2 or 11-3-4) adult rice leaves. Overall cell wall sugar content (A) and relative sugar release (enzymatic saccharification) after hot water pre-treatment (B), values normalized to NH1ox, ±s.e.m, n=3. Letters (a orb) indicate significant difference (p<0.05).

Decreased expression of CCR-like genes has been correlated with increased sugar extractability from cell walls in alfalfa and poplar, an important trait for the production of cellulosic biofuels [34, 39]. We hypothesized that this correlation may also be present in snl6-FN plants. We first determined that the snl6 mutation does not affect the relative cell wall monosaccharide composition in leaves (FIG. 13A). None of the individual sugars tested show a significant difference between the different genotypes (p<0.05). Next, we quantified the total sugar release after hot water pretreatment. Compared to the LG and NH1ox controls, snl6-FN plants showed an increase in sugar release (p<0.05) (FIG. 13B). These results are consistent with previous reports that correlate decreased lignin content with increased sugar extractability [43].

Discussion

The ability of a plant to recognize the presence of a pathogen and mount an effective immune response is fundamental to survival. The defense response must be tightly regulated as each of these responses present a potential fitness cost to the host. The result is a complex network of signaling cascades that govern plant innate immunity. *Arabidopsis* NPR1 and rice NH1 are central regulators of plant innate immunity.

In this report, we describe the identification and characterization of rice Snl6. We identified Snl6 from a screen for mutants that suppress the NH1-mediated lesion mimic phenotype. Notably, while many negative regulators of innate immunity have been identified [36, 44-46], relatively few positive regulators from rice have been characterized to date. By conducting the mutagenesis in an NH1ox background and then screening for suppressors of the lesion mimic phenotype, we were able to specifically target positive regulators, that is, genes that are required for NH1-mediated immunity. Subsequent inoculation experiments confirmed that the suppression of the NH1-mediated lesion mimic phenotype correlated with enhanced susceptibility to the bacterial pathogen Xoo.

Previous reports have demonstrated the potential usefulness of comparative genome hybridization (CGH) or similar comparative genome techniques for plant species [17-23], however routine use of this technique in crop species remains limited. In this report we have successfully combined CGH and fine mapping with RNAi silencing and allelic complementation. In this way we were able to determine that the snl6 mutant phenotype was the result of disruption of LOC_Os01g45200. In cloning Snl6 we generated a population segregating for NH1ox, Xa21 and Snl6. We were able to show that mutations in Snl6 do not compromise resistance mediated by the rice pattern recognition receptor, Xa21 driven by the ubiquitin promoter. These results are consistent with studies from *Arabidopsis* that have shown that the PRR, FLS2, does not require NPR1 to initiate an immune response [38]. Notably, in this population over expression of NH1 confers a similar level of resistance as XA21, highlighting the strength of NH1ox-mediated resistance as previously demonstrated [14].

Snl6 is annotated as a cinnamoyl-CoA reductase (CCR)-like gene, however overall similarity to previously characterized CCRs is low. CCRs catalyze the first committed step of the monolignol biosynthetic pathway. The first identified CCR was from Eucalyptus [47] followed a year later by an orthologue from tobacco [48]. To date, several CCRs have been characterized though their exact role in lignin biosynthesis is still unclear. Studies from *Arabidopsis* and tobacco indicate that down regulation of CCR results in severe developmental phenotypes, including collapsed xylem cells and dwarfism, a decrease in total lignin along with a higher S/G ratio in the lignin polymer, and the appearance of feruloyl tyramines [40-42, 49, 50]. Among the CCR family, a large amount of sequence variability exists, which may contribute to the overall uncertainty about the exact role of CCR. In *Arabidopsis*, two CCRs, AtCCR1 and AtCCR2 have been compared and attributed a role in lignin biosynthesis during development or pathogen attack, respectively. While AtCCR2 is primarily involved in pathogen defense, knockdown experiments have shown that it can at least partially compensate for a downregulated AtCCR1.

To date, we are aware of one report characterizing a CCR-like gene from rice. OsCCR1 was originally identified based on its in vitro interaction with OsRac1. OsRac1 is a GTPase, important for the defense response in rice. While expression of OsCCR1 was induced by a sphingolipid elicitor in suspension cells, no mutant phenotype was observed [31]. Notably, OsCCR1 is dissimilar to Snl6, sharing only 28% identity at the amino acid level.

Here we show that mutations in Snl6 disrupt the NH1ox-mediated constitutive activation of PR genes, providing a mechanism for the role of Snl6 in NH1-mediated resistance. In addition, as Snl6 is annotated as a CCR-like gene, we hypothesized that snl6 mutant lines may contain alterations in the phenylpropanoid biosynthetic pathway. Indeed, we show that disruption of Snl6 leads to less lignin accumulation. Based on these data alone, it is unclear whether Snl6 contributes specifically to NH1ox-mediated resistance or as part of a more general resistance response. However, because Snl6 is highly co-expressed with two additional members of the phenylpropanoid biosynthetic pathway, PAL and 4CL, and because both these genes are induced in NH1 over expression plants, it seems likely that overexpression of NH1 does induce lignin biosynthesis. As lignin is an important defense molecule, providing a physical barrier to pathogen entry into the plant, our results indicate that Snl6 has dual roles in the resistance response: activation of PR genes and lignin biosynthesis.

Lignin contributes to plant structure as well as pathogen defense. Most previously described lignin mutants contain a severe phenotypic detriment [34, 40-42]. Our result, that snl6 mutants contain decreased lignin, is particularly relevant to studies of bioenergy crops because snl6 mutant lines do not display an obvious morphologic phenotype. In addition, we observed a greater than 15% increase in sugar extractability from snl6 mutants as compared to controls. Our results indicate the presence of a previously uncharacterized group of CCR-like genes, alterations in which can alter lignin content without affecting development.

Example 2: Materials and Methods

NH1ox Mutant Screen.

NH1ox seeds were treated with fast neutron (FN) mutagenesis in three batches at 18, 20 and 22 Grays, respectively. This $M_0$ population was grown at the UC Davis rice field and $M_1$ seed from approximately 4,000 $M_0$ individuals was then collected as 400 pools (10 per pool). Approximately fifteen $M_1$ seed from each of the $M_0$ lines were subsequently grown in the field (n=~60,000 $M_1$ seed). The 60,000 $M_1$ lines were sprayed with 10 mM BTH at 5 weeks and 7 weeks and lesion mimic severity was assessed at 10 weeks. BTH treatment of NH1ox plants in the field resulted in a lesion mimic phenotype. Plants that did not develop lesions were called, Suppressor of NH1-mediated Lesion mimic (snl) mutants. snl6-FN (originally named line 11-3) was identified in this screen.

Xoo Inoculations.

Xoo (Philippine race 6, PXO99AZ) inoculations were carried out as previously described [25]. Briefly, 8-week old rice plants were transferred to the growth chamber. Scissors were dipped in a solution of Xoo cells in water ($OD_{600}$=0.5) and then used to clip the rice leaf tip. Growth curves were performed as previously described [36].

Comparative Genome Hybridization.

In collaboration with Nimblegen, we designed a full genome tiling array for rice, ssp. *Japonica* (average one 50-mer probe/146 bp). CGH was conduced following Nimblegen's specified procedures. Briefly, genomic DNA from snl6-FN and NH1ox plants was isolated and the quality of the DNA was assessed via a spectrophotometer and agarose gel electrophoresis prior to sending to Nimblegen. At Nimblegen, the genomic DNA was sheared, labeled and then hybridized to the tilling array. A negative $\log_2$ ratio represents a deletion in the genome of snl6-FN.

Creation of Line BB1-1.

snl6-FN (line: 11-3-2) was crossed to a transgenic line expressing, Xa21 (Ubi Myc-Xa21 (line 7A-8), (Park, Ronald submitted) pollen donor) under control of the ubiquitin promoter, in a kitaake background. The cross was confirmed by testing the F1 progeny (line: BB1) for the presence of Xa21. The F1 progeny was allowed to self-pollinate to create an F2 population (line: BB1-1) that segregated for Xa21, NH1ox, and all 5 deletions identified from CGH.

Fine Mapping:

Individuals from line BB1-1 were grown in the greenhouse and genotyped for the presence of Xa21, NH1ox, and all 5 deletions identified from CGH. Individuals that did not contain Xa21 (as Xa21 also confers resistance to Xoo, Xa21+ individuals were excluded from this experiment) were moved to the growth chamber for challenge with Xoo and lesion lengths were assessed after 14 days. One individual (line: BB1-1-8A) contained NH1ox, was susceptible to Xoo, and showed a recombination event between the two deletions on chromosome 1. Phenotype and genotype were assessed in the next generation (line BB1-1-8A).

Xa21 Effect on Snl6:

Individual progeny from line BB1-1 described above were grown in the greenhouse and genotyped for the presence of Xa21, NH1ox, and Snl6. Plants were moved to the growth chamber for challenge with Xoo and lesion lengths were assessed after 14 days. Primer sequences are listed in Table 1.

TABLE 1

Genotyping primers

| Gene | Forward primer (SEQ ID NO:) | Reverse primer (SEQ ID NO:) |
|---|---|---|
| Xa21 | ATAGCAACTGATTGCTTGG (9) (H3 fraf F) | CGATCGGTATAACA GCAAAAC (10) (3' Xa21 R) |
| NH1ox | TGATATACTTGGATGATG GCA (11) (Ubi-1) | GGACGGCGATGCGC GCGTC (12) (PrNH22) |
| Deletion 1A | AGCAGGAGGGAGAAGAC ACA (13) (Os01g21420_F) | ACCAGGAAGCAAAG CAAAGA (14) (Os01g21420_R) |
| Deletion 1B | GAAGACGAACCGCGT CTG (15) (Os01g45160_F) | GGTGTCACCTCTGA TCACCTG (16) (Os01g45160_R) |
| Deletion 2 | GTTGCTTGTTGGTGGGA ACT (17) (Os02g33730_F) | TCCGTGGGAAAATC AAAGAC (18) (Os02g33730_R) |
| Deletion 3 | TCCTCAGCAGCTTACCA CCT (19) (Os03g56234_F) | TGCGTCGAACAAGA CGATAG (20) (Os03g56234_R) |

TABLE 1-continued

Genotyping primers

| Gene | Forward primer (SEQ ID NO:) | Reverse primer (SEQ ID NO:) |
|---|---|---|
| Deletion 7 | TACACCGGTAATCCGAT GGT (21) (Os07g35810_F) | GGCCCAAGGACTAA GGTCTC (22) (Os07g35810_R) |

Creation of Snl6-RNAi.

A silencing construct for LOC_Os01g45200 (Genbank: Os01g0639200) was created following our previously described strategy [36]. PCR was used to amplify 425 bp from the 3' end of LOC_Os01g45200 (Primers: GAATTCA-GGCTTCGATACGAGCATGT (SEQ ID NO:23); AGATCTGTCGAATGCGACGGAGTAG (SEQ ID NO:24)). This PCR product was confirmed through sequencing and cloned in inverse orientation (separated by ~1000 bp of GUS intron sequence) into a gateway compatible pENTR (Invitrogen) vector. The inverted repeat sequence was then recombined into a modified version of the binary vector Ubi-pC4300 encoding a gene for mannose selection.

Snl6-RGT Allele Identification.

snl6-RGT (RGT6140B_5.1) was identified from the Rice Transposon Flanking Sequence Tag (FST) Database: available at http sundarlab.ucdavis.edu/rice/blast/blast.html. snl6-RGT was crossed with snl6-FN (pollen donor) and the cross was confirmed through PCR with primers specific to the NH1ox transgene (not present in snl6-RGT).

Real-Time Quantitative RT-PCR Analysis.

Real-time reactions were prepared using Bio-RAD Sso-Fast™ EvaGreen Supermix and run on a BIO-RAD CFX96™ Real-time System. Primers were designed using the Beacon Designer program and $R^2$ and efficiency were determined for each primer pair (Tables 2 and 3). When gene expression from a single plant is displayed, error bars represent standard deviation of 3 technical replicates. When multiple plants are combined, data represent biological replicates (each with 3 technical replicates) for each genotype and the s.e.m and number of individuals (n) is reported.

TABLE 2

Real-time PCR primers

| Gene | Forward primer (SEQ ID NO:) | Reverse primer (SEQ ID NO:) |
|---|---|---|
| NH1 | CAGGTGAGAGTCTACGAGGA AGG (25) (NH1_RT_S2) | TTGTCTTTCAGGAGGTGGATT TGC (26) (NH1_RT_AS2) |
| Os01g45190 | GCTATCGGTGACTTCATCAAT ATC (27) (BB190_RT_S1) | AGACTCTGCCAGGTGTTCC (28) (BB190_RT_AS1) |
| Os01g45200 | CACCGTGGACGGTGATGGCAAC GTG (29) (200_RNAi_F2) | GCAACGACGACGTGAAGACGC (30) (200_cDNA_R2) |
| 03g18850 | AGTTCCTGGACGTGGACAAG (31) | TCTCGTCCTTCACCTCCACT (32) |
| 12g36850 | ACGCAGGGAGCGTATACAAG (33) | CACCCTGCTCTTAACCTCCA (34) |
| 02g41650 | GGCCTCCACATCGCTCGC (35) | ACGGCCTCGCGGTCGA (36) |
| Ubiquitin | ATGGCCAACCACTTCGACCG (37) (UBQ5_F) | TAAGCCTGCTGGTTGTAGA CGT (38) (UBQ5_R) |

TABLE 3

Efficiency (E) and R² values for real-time PCR primers

| Primers | E (%) | R² |
|---|---|---|
| 01g45190 | 99.9 | 0.961 |
| 01g45200 (Snl6) | 104.7 | 0.989 |
| 03g18850 (PR10-family) | 99.1 | 0.984 |
| 12g36850 (PR10-family) | 98.3 | 0.986 |
| 02g41650 (PAL-family) | 107.8 | 0.900 |
| NH1 | 91.2 | 0.985 |
| UBQ5 | 105.5 | 0.981 |

Phloroglucinol Staining.

Leaf tissue was collected from plants just before the emergence of the panicle and cleared in a solution of ethanol, lactic acid and phenol (2:1:1) as previously described [27]. Cleared tissue was then soaked in 0.6% Phloroglucinol (in 2:1 ethanol/HCL). Tissue was vacuum infiltrated for one hour and then left in the dark over night. Note: the reported phenotype is dependent on the tissue type, age and health of the plants. Altered phenolic content in snl6 mutant plants was not observed in roots or stems, in plants showing high levels of stress or in young plants.

Sugar Analysis.

Alcohol insoluble residue (AIR) was prepared from ground mature rice leaves and destarched with alpha-amylase (Megazyme). All analyses were done using five mg of destarched AIR. For hemicellulose sugar composition, AIR was treated with 2M TFA at 120 C for 1 h, dried and re-suspended in water. An aliquot was taken for analysis by high performance anion exchange chromatography with pulse amperometry detection (HPAEC-PAD) using a Carbopac PA20 analytical column (Dionex) and monosaccharide standards. Cellulose content was estimated as glucose equivalents using HPAEC-PAD from AIR treated with sulfuric acid (72% w/w) for 1 h at 30 C, then diluted to 4% and incubated at 120 C for 1 h. For enzymatic saccharification, AIR was first pre-treated in water at 100 C for 1 h, then a mixture of cellulase and beta-glucosidase (5% w/w dose, Novozyme) in 0.1M citrate buffer, pH 5.0 was added (reaction volume of 1% total solids); samples were incubated at 50 C for 8 h and an aliquot was then taken to calculate total reducing sugar amounts using the DNS assay.

Sequence Analysis.

Protein sequences were obtained from NCBI, TIGR or the JGI *Brachypodium* resource and compared using the web-based ClustalW software available at www http.ebi.ac.uk/Tools/clustalw2/index.html).

REFERENCES

1. Panstruga, R., J. E. Parker, and P. Schulze-Lefert, *SnapShot: Plant immune response pathways*. Cell, 2009. 136(5): p. 978 e1-3.
2. Clay, N. K., et al., *Glucosinolate metabolites required for an Arabidopsis innate immune response*. Science, 2009. 323(5910): p. 95-101.
3. Cohn, J., G. Sessa, and G. B. Martin, *Innate immunity in plants*. Curr Opin Immunol, 2001. 13(1): p. 55-62.
4. Quentin, M., et al., *Imbalanced lignin biosynthesis promotes the sexual reproduction of homothallic oomycete pathogens*. PLoS Pathog, 2009. 5(1): p. e1000264.
5. Nurnberger, T. and V. Lipka, *Non-host resistance in plants: new insights into an old phenomenon*. Molecular Plant Pathology, 2005. 6(3): p. 335-345.
6. Jones, J. D. and J. L. Dangl, *The plant immune system*. Nature, 2006. 444(7117): p. 323-9.
7. Menden, B., M. Kohlhoff, and B. M. Moerschbacher, *Wheat cells accumulate a syringyl-rich lignin during the hypersensitive resistance response*. Phytochemistry, 2007. 68(4): p. 513-20.
8. Wu, G., et al., *Activation of Host Defense Mechanisms by Elevated Production of H2O2 in Transgenic Plants*. Plant Physiol, 1997. 115(2): p. 427-435.
9. Cao, H., et al., *Characterization of an Arabidopsis Mutant That Is Nonresponsive to Inducers of Systemic Acquired Resistance*. Plant Cell, 1994. 6(11): p. 1583-1592.
10. Cao, H., et al., The *Arabidopsis* NPR1 gene that controls systemic acquired resistance encodes a novel protein containing ankyrin repeats. Cell, 1997. 88(1): p. 57-63.
11. Dong, X., *NPR1, all things considered*. Curr Opin Plant Biol, 2004. 7(5): p. 547-52.
12. Fan, W. and X. Dong, *In vivo interaction between NPR1 and transcription factor TGA2 leads to salicylic acid-mediated gene activation in Arabidopsis*. Plant Cell, 2002. 14: p. 1377-1389.
13. Rairdan, G. J. and T. P. Delaney, *Role of Salicylic Acid and NIM1/NPR1 in Race-Specific Resistance in Arabidopsis*. Genetics, 2002. 161(2): p. 803-811.
14. Chern, M., et al., *Overexpression of a rice NPR1 homolog leads to constitutive activation of defense response and hypersensitivity to light*. Mol Plant Microbe Interact, 2005. 18(6): p. 511-20.
15. Wu, C., et al., *Rice lesion mimic mutants with enhanced resistance to diseases*. Mol Genet Genomics, 2008. 279(6): p. 605-19.
16. Lorrain, S., et al., *Lesion mimic mutants: keys for deciphering cell death and defense pathways in plants?* Trends Plant Sci, 2003. 8(6): p. 263-71.
17. Rostoks, N., et al., *Single-feature polymorphism discovery in the barley transcriptome*. Genome Biol, 2005. 6(6): p. R54.
18. Mockler, T. C., et al., *Applications of DNA tiling arrays for whole-genome analysis*. Genomics, 2005. 85(1): p. 1-15.
19. Kumar, R., et al., *Single feature polymorphism discovery in rice*. PLoS One, 2007. 2(3): p. e284.
20. Gong, J. M., et al., *Microarray-based rapid cloning of an ion accumulation deletion mutant in Arabidopsis thaliana*. Proc Natl. Acad Sci USA, 2004. 101(43): p. 15404-9.
21. Hazen, S. P., et al., *Rapid array mapping of circadian clock and developmental mutations in Arabidopsis*. Plant Physiol, 2005. 138(2): p. 990-7.
22. Bruce, M., et al., *Detection of genomic deletions in rice using oligonucleotide microarrays*. BMC Genomics, 2009. 10: p. 129.
23. Borevitz, J. O., et al., *Large-scale identification of single feature polymorphisms in complex genomes*. Genome Res, 2003. 13(3): p. 513-23.
24. Sung, D. Y., et al., *ARS5 is a component of the 26S proteasome complex, and negatively regulates thiol biosynthesis and arsenic tolerance in Arabidopsis*. Plant J, 2009. 59(5): p. 802-13.
25. Song, W. Y., et al., *A receptor kinase-like protein encoded by the rice disease resistance gene, Xa21*. Science, 1995. 270(5243): p. 1804-6.
26. Lee, S. W., et al., *A type I-secreted, sulfated peptide triggers XA21-mediated innate immunity*. Science, 2009. 326(5954): p. 850-3.
27. Fitzgerald, H. A., et al., *Overexpression of (At)NPR1 in rice leads to a BTH- and environment-induced lesion-mimic/cell death phenotype*. Mol Plant Microbe Interact, 2004. 17(2): p. 140-51.

28. Xu, K., et al., *Sub1A is an ethylene-response-factor-like gene that confers submergence tolerance to rice*. Nature, 2006. 442(7103): p. 705-8.
29. Bignell, G. R., et al., *High-resolution analysis of DNA copy number using oligonucleotide microarrays*. Genome Res, 2004. 14(2): p. 287-95.
30. Ngo, D. M., et al., *A nuclear fragmentation energy deposition model*. IEEE Trans Nucl Sci, 1991. 38(1): p. 1-8.
31. Kawasaki, T., et al., *Cinnamoyl-CoA reductase, a key enzyme in lignin biosynthesis, is an effector of small GTPase Rac in defense signaling in rice*. Proc Natl Acad Sci USA, 2006. 103(1): p. 230-5.
32. Lauvergeat, V., et al., *Two cinnamoyl-CoA reductase (CCR) genes from Arabidopsis thaliana are differentially expressed during development and in response to infection with pathogenic bacteria*. Phytochemistry, 2001. 57(7): p. 1187-95.
33. Kolesnik, T., et al., *Establishing an efficient Ac/Ds tagging system in rice: Large-scale analysis of Ds flanking sequences*. Plant Journal, 2004. 37(2): p. 301-314.
34. Leple, J. C., et al., *Downregulation of cinnamoyl-coenzyme A reductase in poplar: multiple-level phenotyping reveals effects on cell wall polymer metabolism and structure*. Plant Cell, 2007. 19(11): p. 3669-91.
35. Escamilla-Trevino, L. L., et al., *Switchgrass (Panicum virgatum) possesses a divergent family of cinnamoyl CoA reductases with distinct biochemical properties*. New Phytol, 2009.
36. Chem, M., et al., *Rice NRR, a negative regulator of disease resistance, interacts with Arabidopsis NPR1 and rice NH1*. Plant J, 2005. 43(5): p. 623-35.
37. Park, C. J., et al., *Overexpression of the endoplasmic reticulum chaperone BiP3 regulates XA21-mediated innate immunity in rice*. PLoS One, 2010. 5(2): p. e9262.
38. Zipfel, C., et al., *Bacterial disease resistance in Arabidopsis through flagellin perception*. Nature, 2004. 428 (6984): p. 764-767.
39. Jackson, L. A., et al., *Improving Saccharification Efficiency of Alfalfa Stems Through Modification of the Terminal Stages of Monolignol Biosynthesis*. Bioenergy Research, 2008. 1: p. 180-192.
40. Jones, L., A. R. Ennos, and S. R. Turner, *Cloning and characterization of irregular xylem4 (irx4): a severely lignin-deficient mutant of Arabidopsis*. Plant J, 2001. 26(2): p. 205-16.
41. Mir Derikvand, M., et al., *Redirection of the phenylpropanoid pathway to feruloyl malate in Arabidopsis mutants deficient for cinnamoyl-CoA reductase 1*. Planta, 2008. 227(5): p. 943-56.
42. Ruel, K., et al., *Impact of CCR1 silencing on the assembly of lignified secondary walls in Arabidopsis thaliana*. New Phytol, 2009. 184(1): p. 99-113.
43. Chen, F. and R. A. Dixon, *Lignin modification improves fermentable sugar yields for biofuel production*. Nat Biotechnol, 2007. 25(7): p. 759-61.
44. Li, X., et al., *Identification and cloning of a negative regulator of systemic acquired resistance, SNI1, through a screen for suppressors of npr1-1*. Cell, 1999. 98(3): p. 329-39.
45. Peng, Y., Laura E. Bartley, Xuewei Chen, Christopher Dardick, Mawsheng Chern, Randy Ruan, Patrick E. Canlas, Pamela C. Ronald., *OsWRKY62 is a Negative Regulator of Basal and Xa21-Mediated Defense against Xanthomonas oryzae pv. oryzae in Rice*. Molecular Plant, 2008. 1(3): p. 446-458.
46. Park, C. J., et al., *Rice XB15, a protein phosphatase 2C, negatively regulates cell death and XA21-mediated innate immunity*. PLoS Biol, 2008. 6(9): p. e231.
47. Lacombe, E., et al., *Cinnamoyl CoA reductase, the first committed enzyme of the lignin branch biosynthetic pathway: cloning, expression and phylogenetic relationships*. Plant J, 1997. 11(3): p. 429-41.
48. Ralph, J., et al., *NMR characterization of altered lignins extracted from tobacco plants down-regulated for lignification enzymes cinnamylalcohol dehydrogenase and cinnamoyl-CoA reductase*. Proc Natl Acad Sci USA, 1998. 95(22): p. 12803-8.
49. Chabannes, M., et al., *Strong decrease in lignin content without significant alteration of plant development is induced by simultaneous down-regulation of cinnamoyl CoA reductase (CCR) and cinnamyl alcohol dehydrogenase (CAD) in tobacco plants*. Plant J, 2001. 28(3): p. 257-70.
50. Goujon, T., et al., *Down-regulation of the AtCCR1 gene in Arabidopsis thaliana: effects on phenotype, lignins and cell wall degradability*. Planta, 2003. 217(2): p. 218-28.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

All publications, accession numbers, patents, and patent applications cited in this specification are herein incorporated by reference as if each was specifically and individually indicated to be incorporated by reference.

EXAMPLES OF SEQUENCES

```
Rice Sn16 cDNA sequence
                                                      SEQ ID NO: 1
ATGCGGCGGCGCTGCTGCATGGCCACGGGGCGGGCGGCGGCGGCGGCGGCCGGG
TGGCGCCCCTCGGCCGGCGACGCGGACGTCAAGCGCACCGCGGGCGGCGACGGGGCGCG
GCGGGGCCGCGCACCGTCTGCGTCACGGGCGGCATCTCCTTCGTCGGGTTCGCCGTCGTC
GACCGCCTGCTCCGGCACGGCTACACCGTGCGCCTCGCCCTCGAGACCCAAGAGGACCTG
GACAAGCTGAGGGAGATGGAGATGTTCGGCGAGGACGGCCGGCAGCGGCGTGTGGACGGTG
ATGGCGAACGTGACGGACCCCGAGAGCCTGCACCGGGCGTTCGACGGATGCGCCGGCGTG
TTTCACACCTCGGCGTTCGTGGATCCGGGGGGCATGTCCGGCTACACGAAACATATGGCA
AGCTTGGAGGCGAAAGCAGCAGAGCAGGTGATCGAGGCGTGCGTGAGGACAGAGTCCGTC
AGAAAATGCGTCTTCACGTCGTCGTTGCTAGCATGTGTATGGAGGCAAAATTACCCTCAT
GACCGACGGTTTCCTACCATCATCGACGAGAACTGCTGGAGCGATGAGAGCTTCTGCCGT
GACAACAAGCTGTGGTTTGCACTGGGCAAGACGGCAGCGGAGAAGACGGCGTGGAGGGCA
GCCAGGGGTAGGGACCTGAAGCTGGTCACCGTCTGCCCGGCGCTGGTCACCGGTCCGGGA
TTCCGCCGCCGCAACTCCACCGCCTCCATCGCCTACCTCAAAGGGGCTCGCGCCATGCTC
GCCGACGGCCTGCTCGCGACGGCGAGCGTGGAGACGGTGGCGGAGGCGCACGTCCGGGTG
TACGAGGCGATGGGCGACAACACGGCCGGCGGGAGGTACATCTGCTACGACCACGTGGTG
```

```
-continued
AAGAGGCCCGAGGAGTTCGCGGAGCTGGAGCGCCAGCTGGGGATCCCGCGCAGAGCGGCG
GCGGCGGCGGCCGCGCAGGACTCCGGCGACCGGCCGGCGAGGTTCGATCTGTGCAGGCAG
AAGCTGGCGAGGCTCATGTCCACCCGAAGGCGGTGCACGTACGACGACTACTACTCCGTC
GCATTCGACTAG Rice Snl6 protein sequence
                                            SEQ ID NO: 2
MRAALLHGHGGGAAAAAAAGWRPSAGDADVKRTAGGDGGAAGPRTVCVTGGISFVGFAVV
DRLLRHGYTVRLALETQEDLDKLREMEMFGEDGRDGVWTVMANVTDPESLHRAFDGCAGV
FHTSAFVDPGGMSGYTKHMASLEAKAAEQVIEACVRTESVRKCVFTSSLLACVWRQNYPH
DRRFPTIIDENCWSDESFCRDNKLWFALGKTAAEKTAWRAARGRDLKLVTVCPALVTGPG
FRRRNSTASIAYLKGARAMLADGLLATASVETVAEAHVRVYEAMGDNTAGGRYICYDHVV
KRPEEFAELERQLGIPRRAAAAAAAQDSGDRPARFDLCRQKLARLMSTRRRCTYDDYYSV
AFD Sorghum bicolor protein sequence EES03334.1
                                            SEQ ID NO: 3
MGVLRSTQSLQAEVDELRAALGLSGGGHGEAAAGGGWRRSAGRGHADAKRAPGGDAGAG
AAARAVCVTGGISFVGFAVVDRLLRHGYTVRLALETQEDMDKLRENEMFGEDGRDGVWTV
MANVMDPESLHRAFDGCAGVFHTSAFVDPGGMSGYTKHMATLEAQAAERVIEACVRTESV
RKCVFTSSLLACVWRQNYPHDRRCPTIIDESCWSDESFCRDNKLWFALGKTAAEKAAWRA
ARGRDLKLVTICPALVTGPGFRRRNSTASIAYLKGARAMLADGLLATANVETVAEAHVHA
YEAMGDNTAGGRYICYDHVVKRPEEFAELERQLGLPGGATAARGSDDDRPARFELCKRKL
SRLMSSRRRCTYDTYYSVAFD Maize protein sequence ACR34585.1
                                            SEQ ID NO: 4
MGVLRSTQSLEAEVDELRAALLAGGWRRSAGHADAKRAPRGDAGGAAARAVCVTGGISFV
GFAVVDRLLRHGYTVRLALETQEDMDKLREMEMFGEDGRDGGVSTVMANVMDPDGLRRAF
DGCAGVFHTSAFVDPGGMSGYTKHMAALEAQAAERVIEACVRTESVRKCVFTSSLLACVW
RQDYPHDRRCPTTIDESCWSDESFCRDNKLWFALGKTAAEKAAWRAARGRDLKLVTICPA
LVTGPGFRRRNSTASIAYLKAGARAMLADGLLATANVETVAEAHVHAYEAMGDNTAGGRY
ICYDHVVKRPEEFAELERQLGLPGGAAPAPAHGSDDRPARFELCKRKLSRLMSSRRRCAY
DTYYSVAFEV Brachypodium protein sequence
                                            SEQ ID NO: 5
NFANHTPPPGTTPPGETSSLQEGRAPAGVAASSRARGGMGVLRSTQSLQAEVEEMRAALL
LPGGAAAGWKPSGGDAGGEEGAAGPRTVCVTGGISFVGFAIVDRLLRQGYTVRLALETQE
DVDKLREMEMFGEDGRDGVWTVMANVMDPESLHRAFDGCAGVFHTSAFVDPGGMSGYTKH
MASLEAKAAERVIETCVRTESVRKCIFTSSLLACVWRQNYPHDRRGPSIIDENCWSDESF
CRDNKLWFALGKTAAEKAAWRAARGRDLKLVTVCPALVTGPGFRRRNSTASIAYLKGSRD
MLAEGVLATANVETVAEAHVRAYEAMGNNTAGGRYICYDHVIRRAEDFAELERQLGIPSR
TAASVLQSGDEDRPARFELCKRKLARLMSSRRRCTYDDYYYSVTSP Rice Os05g50250 protein sequence
                                            SEQ ID NO: 6
MGVLRSTQSMEAEVEEMRAALALAPLGRHGAWRSGAAAKREAGAEEGAAPEARTVCVTGG
ISFVGLAVVDRLLRHGYAVRLALETQEDLDKLREMEMFGENGRDGVWTVMANVMDPESLN
QAFNGCVGVFHTSSLIDPGGISGYTKHMAILEARAAEQVVEACVRTESVRKCVFTSSLLA
CVWRQSYPHHRRRFPAIIDESCWSDESFCRDNKLWFALGKTMAEKAAWRAARGRDLKLVT
ICPALVTGPGFRRRNSTPSIAYLKGAHAMLAEGLLATADVERVAEAHVRVYEAMSGGGAA
GGRYICYDHVVRRGEEFAELQRQLGLPITGVAAASRPGYSDDGDVGGDGRFALCNGKLAR
LVSSRRRCTYDVYYPASYD Rice Snl6 genomic DNA sequence
                                            SEQ ID NO: 7
ATGCGGGCGGCGCTGCTGCATGGCCACGGGGCGGGGCGGCGGCGGCGGCGGCGGCCGGG
TGGCGCCCCTCGGCCGGCGACGCGGACGTCAAGCGCACCGCGGGCGGCGACGGGGGCGCG
GCGGGGCCGCGCACCGTCTGCGTCACGGGCGGCATCTCCTTCGTCGGGTTCGCCGTCGTC
GACCGCCTGCTCCGGCACGGCTACACCGTGCGCCTCGCCCTCGAGACCCAAGGTCAGCTC
CAAATCCAGCTCACCCCCACATCTTTTACCGTTTACCTGTTCGATTACCTCCTTTGCCTT
GTTTGGCTGTTTCGCTTCTGTGTCACCGACATGTGGGCCCCGGTCGCCACATGTATCTCA
AAGCCCCGGCCACTTGTGCCAATACATTCCACGTATTTTTATTATTTTTATATACCTCGGC
AAAAAAAAACAAACATGAAAAAACAAAAACGCTCGTGCCTAGCATGACGTACCCCTTCGCT
AGTTCGCTGTATCCAATTTCTGGACTTTATCTCGCAGCAGTAGATTTTACTTCTACCAGC
TTATTGAGCCGATCAGTCTTCCAATCCATCTTAATTACCACTCGTTTTTGGACAAAAGGC
AAGCGACTTCCCAGCATAAACCAAGCTTAGTTGCTGTTCAAGCCGGATTAGCAGATACTC
TGCGTCTCCTCCCGAAGTGTTGTTGGGGATGGAACCTTGCCACCTACCGCTGCACTGCGG
GTTTGGTGTGCTACCTGCAGTCCGGTCACCATTTCGTCACATCTCCATAGACCGGTTGCT
AGCTTGGAGTAGCTAGGAACTACTACGCTGCATCTTCCCGTCAGTAGAATTTGCTTTCGT
TGGATAATGGCGTAACGCTCTTTGACGGTGTATATCCATTTGCGAATAGAGACCAAACTA
AAAAAAAAAAATATTGGCATAATGCTCTGCTCGGGCTGGTGGGTGGTATGGCAGCCACTTT
CCTATGCACAGTGTGCATGTAGCCGTGAGAGTATACCTAATGATGATTGCTTTTATGCTT
TGGTGAATATAACCAACTTAATTACCTACTTGGAAATGACAGACCGAAAGAAACGTGCGA
AAGCTAAAGAGAGGAACATATACGTTTATGTCTAATTCGCCACACACAAGGAAAAACGGA
AGAAAAAAACAAATGCTAACAAGGAGTAGGATTGATGGGAGGTGGTAGCTAGACTGAATT
AGTTTAAGACGTACGCAACCATCTCTATGATCGATCAGCGTTGAACATTTGACTACTCGT
ATATATAAAGCTACCGGGCGTATGATTTCCTCGTGTAGTAGTTAGTTATTCTCGCATTCG
TTTTTTCCTCGTGCTATATGCACAATCTTTGGATGCATTCAAAACATTCTGATTGTGACT
TTCTCCATATACCAATGGGCTCATGCTTATGGCGTAACATTAAACTTTTCGCCGGTTTTT
```

-continued

```
ATTCTTGTTCTGGTGGTCAGCCGGTTTCTTGGAAAGAGGAAATTGATCGTAGTTTCAAAG
TCTCCTATACGACTCGTCCAGTTGGGGATGAAACAATCTACAAATCAAACACTAGCAGAG
ACGTACGCAGAATTTTTTTTTCCACTGGCAGCACCATTTTTCTTTGACCCGAGGTAGAAA
TCTTCAGGTCTACCACATCATGATTAGATTTCAACCAACCAGTGCTCCAATTCGGATACC
CATTTTAACATTGCGCCACTAATTAGTCAGCTTTGTGTTGCTTAGTTGAGCCATACTTTA
CGCGTTCTGATCCTTCACATCAGCTAACAAATCCAATCCTTCCCCTGAACCAAAATCTTT
CAGTACTGCTCCCTTCAATTCCCTAGCAAGAAAGCAGAGAACCTTTCGACAAACAAATAG
TGTTGATACTAATTATAAGTGGGTGCTGGACTTCTGATAGCTTCGTTTCAACAGTCTACA
CCCAAGGGCCATTAGGAAAATTTATCTGATGATAGCTTAGCTCCAATCTTAATCTGGAAC
AACATGTCTGGTCCATTAGGCCTCCACTGGAATAGAGGAATATCACGGGAGTTGAACTAA
TTCTTGTGAAAATCCTGTAGAAGTCATGCCTTTATCTTTATGCTATCACTACCATTCTCT
AAGTCATCGCGGATAAGAAACCATGGGCAAGAAAATTTTCAGAATATCAAAAAGATAAAA
TCCTCTCTCCGGTTTCCCAGCCAGCTACGAATAGTTGGAAACACACCTGCTGCTTGGCTA
TGCTTATAATAGTGGAACATGATTCATATTTCTGGTTTTCAAATGGAGTCAGGTGAGAAG
GATGGAACGAGATTATTGATAAAGTACCGTTCCAAAAACGTTCTTATCCTTATCGGACAA
TTATCAATGATAGATAACAGAAAGTAAAATCACACGGCATCATCGCTATTATTTTATTAA
AGCAACATGGCTTCTTTTTTTTTGTGAGTATTCATGCAACCATCGTAATCTTGACGTGTA
ATAATTTGGCTTATTGCTATTTGCTACATCGCAGAGGACCTGGACAAGCTGAGGGAGATG
GAGATGTTCGGCGAGGACGGCCGGGACGGCGTGTGGACGGTGATGGCGAACGTGACGGAC
CCCGAGAGCCTGCACCGGGCGTTCGACGGATGCGCCGGCGTGTTTCACACCTCGGCGTTC
GTGGATCCGGGGGCATGTCCGGCTACACGGTGAGTGCACCAAACTCGGTCCCTAACCTT
AAGATCCTCGCAACTACTACACCTACCTATGTTATGTGTTCCCTAATGCTGTCACAGAAG
TCACTAAGTAAGTTAGTTATGTGTTCCCTAATGCTGTCATATAGAAGTCACTAAATAAGT
TAGGTTAGTAAAATATAGAAAAAATCATGCAAACAAAACAGAGTGAACTTGAAGAGAATG
GCGGAAAACAGAGTATATATGCTCCATCTAACATTCTAACTCAAGGCGCAACTGAACATC
AAAGATTGATGTTGAATGTTTGGTGTACTATAAAAAGAGCAATATTTATTTATGGTCGTTA
AGAAGGTATCAAGAAGTACTACAATTTTACTAGAAGACACTAAATTTTACAATTAAAAAA
AGATACCTCCTGATACACCATAAAATAACTCGTAAAAGGAACATTGCGATTTTCTTTGTG
GTGATGTGGTGGGGACCCAGTAACAGTCTGAACTTCTGGAAATCAAGCAATTAATTGACA
CATAACGGCGTTCGGGAATTTTTGAAGCCAATGGACATAGATCATTTTCGTAATTAATGG
CATGCACATCACAGAGCCTCAGACATCTGGCCCAGAGAAATTTGTACAGTTGAGCTGTAG
AGTTTGCATCTACATGTACATGGCCTTTGGTACTGCACGTGGAGGCACTCATGCCTCAAA
ATTCAGAAAGATTTGTAAGACCGAGTGACGAGACTCTGTAGTTCGTGTACCACACGGGG
AAGATTCTGCTCATTCTTGGCTTCTCCTCCCAAGAGACACCAAATAGTTTATGGTACCCG
TTATCTAGAAACGTTGGGCGCTCGGGTGTCCATCACAGATGTTAACGGTTATACCTTCCA
TGGTTACTTAAAAACTGAGACCTTGCTGATTGTCGATTCCATTGGTCGTACAGTAGTATC
AAGATTTCAAAAATGACAAACCAGTACTATTGACTGATGTGAAGAGCGGCAGATGCCATA
AAACTAGCCTTATTTCGAGCAGACTTAATAAAAAAAGGGTTTATAGAAAAAGGCTCAATC
ACCAACTCGTACCTTCAAGGATTATTTTGTTTACGAGCCAATGTCTTGTTTGTTGCCAAA
GGCAGGGTGGGAGAGGATCTTGAGGCTGGACAGTCCTCCTTGTCGCCCTTTCGTTGACAT
TTTGCCAAACCTGAAGTCCTCCTGATGGGAGCAGGTTGTAACTGGTAGTCCTGCCTATGC
AGATGGTCTTGCACCTATCTGATCCATGAAGTAGAGCTTCCGGAGCACAGCATTGGTGGG
CGCACGCCTGTCAACTCCGTCACCTAATTCATTGACAGAAAATCGCTTGTCCATAGCAGG
GGACCGGGTTTATTATCTGATAAGAACGGGTAATCAGGTAGGATTAGTATCTGAGTGTGA
TGAGAGTCCGCATTGCAGCAAGAGTTGGACAATACAACCACCGAATCCACTTCGGTTGGG
TACTTCCAAGCAGCCGTCAGAATCATGACGACCTTAGTGTAACCAAGGCGATTAAAGAAC
AGAGATGCCATCCAGTTGCGTCCTACTCTGCAACAATATATACTCCCTCTCTTTTAGATT
TATTAACATATATATAAATATAGGCAATATTATAAAATCTTATATTGTGAAATGCACAAT
AGAGGGAGTATGCTAGTAATAGGCTTTATTTTACTGTTCTTGAATACCTTTATTTTTTTT
ACCATTCTTGTTCCACACAATATAACCTCTTTTTAATGGAAGAAATTTGCTGCAATTTGG
AGGAAATGAACTGGTTCAATGAAAATCCTGTAAAATTTATGCGTTTCAAAGTAGCCCTAC
GTTCGATTTTGCTATATATTTGTCGACAAATTTTCCCCTAAAAATTTAACAGATGTAATT
ACAGTACAATCGTAGTGTAATTACACTATAACTTGCATGTAATTACACTGTAACTATAGT
GTAACTTGTATGTAACTTTCAAAAATCTCTCCGTAATATGTTATTTCGATAAAATGGAGG
TCGTGGGAACAAATTCTTTCACATATGTGTGTACTATGATTTGTTTTCTTCCTCACCAAA
ACAAATCTTGTAATAGATCTAACAATTCAAAATTATGTGAAACTTACATATAAGTTACAC
TGTAGTTACATGCAAGTTACAGTGTAATTACATATATGTTACAGTGTAATTACATTATGA
TTGTATTATAATTACATCTGTCAAATTTTTAGGAGAAAATTTGTCAACAAATGTATAGGT
AGTCCCCCCTACGTTTGGTATCTCAATCACACTAGTGTTTATCATTTATCTGCAGTAAGA
GCCTATTGTAGCTAAAATAAACCTTACCAAATTTTGGTATTGCCAAAATTTTGGCAAGAT
GACAATATTGCGAAAATTTTGGCAGGATATCTTATGTATTTACTTAATTTGGCAACAAAC
TAAATATAGATATTTTTAACAACTTTACATTAAAAAAATGGTATGGTTGAAAATAGCAT
CAAAGTGAACGGGCCTGATTTTCGCTAGTGGACCGTTCGCTCTCACCCATCATTCCTGGT
AGTCAATTCTTGTGTAGTCATGGTAATTTGTTGTTTAGTAGCGATTGGGCGTACGATTGA
GGCGGTGTAATTAACTTTTTCCCTGTTAATGTCCAACTCTCGAACAGAAACATATGGCAA
GCTTGGAGGCGAAAGCAGCAGAGCAGGTGATCGAGGCGTGCGTGAGGACAGAGTCCGTCA
GAAAATGCGTCTTCACGTCGTCGTTGCTAGCATGTGTATGGAGGCAAAATTACCCTCATG
ACCGACGGTTTCCTACCATCATCGACGAGAACTGCTGGAGCGATGAGAGCTTCTGCCGTG
ACAACAAGGTGAGTTTGTTACTGTATTAAAAAAAAAGGAGGGTTTGTTCAGTGACACGG
AAGCGCACTTGCAATGGTGGATGCATAAGCATATTTTATCACCCACCAACTGAATCTTTT
TTTTTTCTTGTGGAAAATTTGTGCAATCTAATGACTTTCTGGATAAACTTTTCAGCTGTG
GTTTGCACTGGGCAAGACGGCAGCGGAGAAGACGGCGTGGAGGCAGCCAGGGGTAGGGA
CCTGAAGCTGGTCACCGTCTGCCCGGCGCTGGTCACCGGTCCGGGATTCCGCCGCCGCAA
CTCCACCGCCTCCATCGCCTACCTCAAAGGTACACTACAGGCTTCGATACGAGCATGTAA
ACTACGATCGGAGAAAGGAACATGGTGTGCCTTTGTGCTTGTGCAGTACACACTGACATG
TCTTGCGTGTCGACAGGGGCTCGCGCCATGCTGCCGACGGCCTGCTCGCGACGGCGAGC
GTGGAGACGGTGGCGGAGGCGCACGTCCGGGTGTACGAGGCGATGGGCGACAACACGGCC
GGCGGGAGGTACATCTGCTACGACCACGTGGTGAAGAGGCCCGAGGAGTTCGCGGAGCTG
GAGCGCCAGCTGGGGATCCCGCGCAGAGCGGCGGCGGCGGCCGCGCAGGACTCCGGC
GACCGGCCGGCGAGGTTCGATCTGTGCAGGCAGAAGCTGGCGAGGCTCATGTCCACCCGA
AGGCGGTGCACGTACGACGACTACTACTCCGTCGCATTCGACTAGATATCTAGCTAGGCT
```

-continued

```
AGGCAAACTGGCGAGCACCACCGTGCAATGGCTTGCAGCACTGCACCAATGATGGATCAT
CTGGGTTGGGTTTTGCCTGAAGGGTGCAAGAGGACGAAGTCGTAGTGGATGGAAGA
AGAGTGTGTGACATCATGTACATAGTGCGATCTTGTAGGCTGTTTGATGCATCAATAAAG
CTTGATCGAGCCCCATTTTTTGGCTA
```

What is claimed is:

1. A method of reducing the amount of lignin in a plant selected from the group consisting of rice, sorghum, maize and *Brachypodium*, the method comprising:
   genetically modifying the plant to disrupt expression of a target endogenous suppressor of NH1-mediated lesion formation 6 (Snl6) gene that encodes a Snl6 polypeptide,
   wherein the endogenous Snl6 gene encodes a polypeptide comprising an amino acid of SEQ ID NO:2 when the plant is rice; the endogenous Snl6 gene encodes a polypeptide comprising an amino acid of SEQ ID NO:3 when the plant is sorghum; the endogenous Snl6 gene encodes a polypeptide comprising an amino acid of SEQ ID NO:4 when the plant is maize; or the endogenous Snl6 gene encodes a polypeptide comprising an amino acid of SEQ ID NO:5 when the plant is *Brachypodium*; and
   selecting a plant that has reduced lignification relative to the wildtype plant in which expression of the endogenous Snl6 gene is not disrupted.

2. The method of claim 1, wherein the step of disrupting expression of the endogenous Snl6 gene in the plant comprises knocking out the endogenous Snl6 gene.

3. The method of claim 1, where the step of disrupting expression of the endogenous Snl6 gene comprises introducing an expression cassette into the plant, wherein the expression cassette encodes a polynucleotide that hybridizes to the Snl6 gene and inhibits expression of the gene.

4. The method of claim 1, wherein the endogenous Snl6 gene is mutagenized to genetically alter the plant to disrupt expression of the endogenous Snl6 gene.

5. The method of claim 1, wherein an endogenous promoter upstream of the endogenous Snl6 gene that controls expression of the endogenous Snl6 gene is mutagenized to genetically alter the plant to disrupt expression of the Snl6 protein encoded by the endogenous Snl6 gene.

6. The method of claim 3, wherein when the plant is a rice plant, the disrupting step comprises introducing into the plant a recombinant expression vector that encodes a polynucleotide that is complementary to all or a portion of a nucleic acid sequence of SEQ ID NO:1 or a complement thereof, and, wherein the polynucleotide is capable of inhibiting production of a protein encoded by SEQ ID NO:1.

7. The method of claim 3, wherein when the plant is a rice plant, the disrupting step comprises introducing into the plant a recombinant expression vector that encodes a polynucleotide that is complementary to a portion of SEQ ID NO:7 or a complement thereof, and is capable of inhibiting production of a protein encoded by SEQ ID NO:7.

8. The method of claim 3, wherein the polynucleotide encodes an siRNA, an antisense polynucleotide, a microRNA, or a sense suppression nucleic acid.

9. The method of claim 1, wherein the plant is rice.

\* \* \* \* \*